(12) United States Patent
Kanda et al.

(10) Patent No.: US 7,175,985 B1
(45) Date of Patent: Feb. 13, 2007

(54) METHOD OF DETECTING VARIATION OR POLYMORPHISM

(75) Inventors: Hidetoshi Kanda, Tochigi (JP); Tsugunori Notomi, Tochigi (JP); Kentaro Nagamine, Tochigi (JP); Toshihiro Yonekawa, Tochigi (JP)

(73) Assignee: Eiken Kagaku Kabushiki Kaisha, Tokyo (JP)

( * ) Notice: Subject to any disclaimer, the term of this patent is extended or adjusted under 35 U.S.C. 154(b) by 348 days.

(21) Appl. No.: 10/129,637

(22) PCT Filed: Aug. 2, 2002

(86) PCT No.: PCT/JP00/07816

§ 371 (c)(1),
(2), (4) Date: Aug. 2, 2002

(87) PCT Pub. No.: WO01/34838

PCT Pub. Date: May 17, 2001

(30) Foreign Application Priority Data

Nov. 8, 1999 (WO) .................... PCT/JP99/06213
Apr. 28, 2000 (JP) .................... 2000-134334

(51) Int. Cl.
*C12Q 1/68* (2006.01)
(52) U.S. Cl. .................... 435/6; 435/91.1; 435/91.2; 536/23.1
(58) Field of Classification Search .................... 435/6, 435/91.1, 91.2; 536/23.1, 24.33
See application file for complete search history.

(56) References Cited

U.S. PATENT DOCUMENTS

| | | | |
|---|---|---|---|
| 4,683,202 A | 7/1987 | Mullis | |
| 5,270,184 A | 12/1993 | Walker et al. | |
| 5,525,462 A | 6/1996 | Takareda et al. | 435/6 |
| 5,595,891 A | 1/1997 | Rose et al. | 435/91.5 |
| 5,612,199 A | 3/1997 | Western et al. | 435/91.1 |
| 5,874,260 A * | 2/1999 | Cleuziat et al. | 435/91.2 |
| 5,981,174 A * | 11/1999 | Wolf et al. | 435/6 |
| 6,025,139 A | 2/2000 | Yager et al. | 435/6 |
| 6,033,881 A | 3/2000 | Himmler et al. | 435/91.2 |
| 6,277,607 B1 * | 8/2001 | Tyagi et al. | 536/23.1 |
| 6,410,278 B1 * | 6/2002 | Notomi et al. | 435/91.2 |
| 6,743,605 B1 | 6/2004 | Rabbani et al. | |
| 2001/0039334 A1 * | 11/2001 | Wright et al. | 536/23.1 |
| 2003/0104460 A1 | 6/2003 | Rabbani et al. | |
| 2003/0165936 A1 | 9/2003 | Rabbani et al. | |
| 2003/0165938 A1 | 9/2003 | Rabbani et al. | |
| 2003/0165939 A1 | 9/2003 | Rabbani et al. | |
| 2003/0170681 A1 | 9/2003 | Rabbani et al. | |
| 2003/0170682 A1 | 9/2003 | Rabbani et al. | |

FOREIGN PATENT DOCUMENTS

| | | | |
|---|---|---|---|
| EP | 0549107 A1 | 9/1992 | |
| EP | 0971039 A2 | 6/1999 | |
| EP | 1 020 534 A1 | 7/2000 | ................ 435/91.2 |
| WO | WO 96/01327 | 1/1996 | |
| WO | WO 99/66071 | 12/1999 | |

OTHER PUBLICATIONS

Karin Dilger, Zhichang Zheng, Ulrich Klotz. Lack of drug interaction between omeprazole, lasoprazole, pantoprazole and theophylline. 1999. J. clin. Pharmacol. 48:438-444.*
Domingo et al. High frequency of mutations at position 2144 of the 23S rRNA gene in clarithromycin-resistant *Helicobacter pylori* strains isolated in Spain. Journal of Antimicrobial Chemotherapy. 1998. vol. 41:573-574.*
Notomi et al., "Loop-Mediated Isothermal Amplification of DNA," *Nucleic Acids Research* 28:e63 i-vii (2000).
Walker et al., "Strand Displacement Amplication—An Isothermal, *In vitro* DNA Amplification Technique," *Nucl. Acids Res.* 20(7):1691-1696 (1992).
Stratagene Cataloge, "Gene Characterization Kits," p. 39 (Feb. 1988).
Lizardi et al., "Mutation Detection and Single-Molecule Counting Using Isothermal Rolling-Circle Amplification," *Nature Genetics* 19:225-232 (1998).
Whitcombe et al., "Detection of PCR Products Using Self-Probing Amplicons and Fluorescence," *Nature Biotechnology* 17:804-807 (1999).

* cited by examiner

*Primary Examiner*—Teresa E. Strzelecka
*Assistant Examiner*—Heather G Calamita
(74) *Attorney, Agent, or Firm*—Nixon Peabody LLP

(57) ABSTRACT

The method of the present invention is based on a method wherein a nucleic acid is synthesized utilizing the hybridized 3'-end, which is synthesized by complementary strand synthesis, on a specific region of a target nucleotide sequence existing as the nucleotide sequence of the same strand as the origin for the next round of complementary strand synthesis. The hybridization to a specific region, which region is searched for mutations and polymorphisms, is repeatedly carried out according to the present invention. Thus, mutations and polymorphisms in a target nucleotide sequence are exactly copied to the reaction products.

22 Claims, 17 Drawing Sheets

Figure 6

Target template
Template comprising single-nucleotide mismatch
No template

SEQUENCE LISTING

```
<160> NUMBER OF SEQ ID NOS: 15

<210> SEQ ID NO 1
<211> LENGTH: 57
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 1
gggaacccat aacaaattac ttaaaaacct gtgttctttt actttctcca aaatatc        57

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 2
agggttgttg atgtccatc                                                  19

<210> SEQ ID NO 3
<211> LENGTH: 65
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 3
cgggaaataa tcaatgatag tgggaaaata tgcttttaat ttaataaatt attgttttct     60
cttag                                                                 65

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 4
ccagagcttg gcatattgta tc                                              22
```

<210> SEQ ID NO 5
<211> LENGTH: 210
<212> TYPE: DNA
<213> ORGANISM: Homo sapiens

<400> SEQUENCE: 5

```
ccagagcttg gcatattgta tctatacctt tattaaatgc ttttaattta ataaattatt      60
gttttctctt agatatgcaa taattttccc actatcattg attatttccc gggaacccat     120
aacaaattac ttaaaaacct tgcttttatg gaaagtgata ttttggagaa agtaaaagaa     180
caccaagaat cgatggacat caacaaccct                                      210
```

<210> SEQ ID NO 6
<211> LENGTH: 46
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 6

```
ccgggaaata atcaatgtaa tttaataaat tattgttttc tcttag                     46
```

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 7

```
cgggaaccca taactgttct tttactttct cc                                    32
```

<210> SEQ ID NO 8
<211> LENGTH: 42
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 8

```
caggaaccca taacaaatta cttagtgttc ttttactttc tc                         42
```

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 9

```
caggaaccca taacaaatgt gttcttttac tttctcc                               37
```

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 10

```
ccgggaaata atctaattta ataaattatt gttttctctt ag                    42

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 11
cgggaaccct gttctttac tttctcc                                      27

<210> SEQ ID NO 12
<211> LENGTH: 43
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 12
ctgggaaata atcataattt aataaattat tgttttctct tag                   43

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 13
caggaaccca tatgttcttt tactttctcc                                  30

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 14
gatagtggga aaattattgc                                             20

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 15
caaattactt aaaaccttg ctt                                          23
```

METHOD OF DETECTING VARIATION OR POLYMORPHISM

This application is a national stage application under 35 U.S.C. § 371 of PCT Application JP00/07816 filed Nov. 7, 2000, which claims priority of both PCT Application JP99/06213 filed Nov. 8, 1999, and Japanese Application 2000-134334 filed Apr. 28, 2000.

TECHNICAL FIELD

The present invention relates to methods for detecting mutations and polymorphisms in nucleotide sequences.

BACKGROUND ART

Mutations in gene regions may cause mis-sense mutations accompanying changes in translated amino acids, silent mutations without any change in the amino acids, and frame shift mutations, wherein the translation frame is shifted due to deletion or insertion of nucleotide(s). Non-sense mutations, wherein a stop codon is generated at incorrect location, are also included as mis-sense mutations. In addition, mutations in gene regions also have the potential of leading to gene translation abnormalities through splicing abnormalities and such. Many of these mutations, other than silent mutations, are accompanied by structural or functional changes in translated proteins.

Moreover, abnormalities in expression regulatory regions have the risk of affecting the expression regulatory mechanism of proteins.

Among differences in the nucleotide sequence of nucleic acids, mutations that are present at a frequency of 1% or more in a certain population are particularly referred to as polymorphisms. A population refers to a population that can be distinguished by geographical isolation or subspecies. For example, even in the case of a mutation that occurs at a frequency of less than 1%, in Japanese, if that mutation is found at a frequency of 1% or more among other races, it is not a mutation, but rather a polymorphism.

Among these polymorphisms, polymorphisms due to insertion, deletion, or displacement of a single nucleotide are particularly referred to as single nucleotide polymorphisms (hereinafter, abbreviated as SNPs). SNPs are of high profile because these are mutations most frequently appearing in the human genome.

Since polymorphisms are spread throughout a population at a fixed frequency, they are considered not to accompany any changes in phenotypes or only changes of such phenotypes that influence phenotypes called constitution, and not those that are particularly disadvantageous for survival (reproduction). For example, predispositions to typical adult diseases, such as diabetes, rheumatism, allergies, autoimmune diseases, obesity, and cancer, are suggested to be determined by polymorphisms when the disease is governed by genetic characteristics. Further, drug metabolism, human leukocyte histocompatibility antigens (hereinafter abbreviated as HLA), and such are also governed by polymorphisms. Moreover, the majority of these polymorphisms are revealed to be SNPs.

Since polymorphisms have these characteristics, like the microsatellite polymorphisms, they are used to determine disease-associated genes by chromosome mapping, linkage analysis, and such. SNPs are present at a rate of one every 300 to 600 nucleotides. Thus, use of SNPs enables construction of a detailed map which is expected to facilitate gene determination.

Moreover, much information is expected to be obtainable by gathering information relating to polymorphism locations and fluctuations, and analyzing their correlation with certain phenotypes. For example, side effects of a drug may be prevented through the discovery of SNPs related to such side effects of the drug. By overcoming these side effects, numerous drugs whose practical application has been abandoned may be reevaluated as safe drugs.

In the case of bacteria and viruses, the subtypes of hepatitis C virus (hereinafter abbreviated as HCV) and such are classifications based on the characteristics of a nucleotide sequence commonly found at a fixed ratio, and thus, these subtypes and such also can be considered as polymorphisms. Mutation analyses investigating the genotypes of such polymorphisms are referred to as typing.

Therapeutic efficacy of α-interferon on HCV differs according to particular subtypes. Therefore, typing provides important information useful in selecting methods for the treatment. Further, pathogens beside HCV, such as influenza virus, malaria pathogens, and *Helicobacter pylori*, are also demonstrated to be pathogens with different therapeutic efficacy according to the subtypes. Thus, typing provides important information for determining the mode of treatment for these pathogens, too.

In contrast to polymorphisms, mutations found at a ratio less than 1% are mutations that do not spread throughout a population in the case of humans, and nearly all of them can be mentioned as mutations-involved in some kind of disease. Specifically, these mutations correspond to those found in hereditary diseases. In addition, some of the mutations found in individuals are also associated with disease, such as mutations found in association with cancer and so on. The detection of such mutations provides decisive information in diagnosing the corresponding disease.

Whether or not the nucleotide sequence of a certain gene differs from the predicted nucleotide sequence can be confirmed by hybridization of the complementary nucleotide sequence. More specifically, hybridization with a primer or probe is used.

For example, PCR primers are only able to act as primers when the target nucleotide sequence has a nucleotide sequence that is complementary to the primer. Based on this principle, a target nucleotide sequence can be examined to determine whether or not it is complementary to the primer, using the PCR amplification product as an indicator. However, there are several problems with this method of confirming nucleotide sequences based on PCR. First, the checking mechanism of the nucleotide sequence by the primer is incomplete. Methods for detecting single nucleotide differences by amplification reaction of PCR methods have been considered (allele-specific PCR, Nucleic Acids Res. 17: p. 2503, 1989; Genomics 5: p. 535, 1989; J. Lab. Clin. Med. 114: p. 105, 1989). However, as was reported by S. Kwok et al. (Nucleic Acids Res. 18: p. 999, 1990), when using a primer with a single nucleotide difference, the reaction proceeds at about 0.1% to 85% (which differs depending on the difference in the sequence) per amplification cycle as compared with a completely complementary primer. In other words, complementary strand synthesis frequently occurs even if the nucleotide sequence is not completely complementary with the primer. Consequently, in order to distinguish single nucleotide differences using allele-specific PCR, artificial insertion of another mismatch at another location has been shown to be necessary. However, in this case as well, conditions must be precisely set according to the sequence difference, which has not become a general technique. Thus, it is difficult to identify single nucleotide differences, such as SNPs, by PCR under ordinary conditions.

In other words, methods wherein nucleotide sequences with slight differences are detected based on hybridization of a complementary nucleotide sequence have the potential of being inaccurately detected. According to the PCR method, products formed by inaccurate detection do also function as complete templates, and thus, these products trigger an exponential amplification. The problem of using conventional PCR method to detect slight nucleotide sequence is that, despite the possibility of inaccurate detection, a high degree of amplification occurs based on the inaccurate detection.

The second problem of the PCR method is that primers for only two regions can be configured due to the principle. Thus, when a plurality of genes composed of similar nucleotide sequences are present in the same sample, mutations and polymorphisms of the genes is extremely difficult when the presence or absence of amplification products based on PCR is used an indicator. This is because the PCR reaction proceeds when the primer hybridizes to one of the genes, even if a gene with mutation exists in the sample.

For example, a primer for detecting a mutation of a certain gene in a family gene, such as human CYP2C19, acts as a primer on other genes as well. FIG. 6 depicts mutually similar nucleotide sequences found in the human CYP2C19 family. As suggested from the Figure, a primer for detecting mutation of a certain gene also acts as a primer for other genes of the wild type. Under such conditions, it is difficult to simultaneously identify the similar gene and detect the mutation with only two regions.

To solve the two problems described above, so called PCR-dependent mutation detection techniques have been reported wherein the target gene is specifically amplified by PCR, and then the mutations are detected using a probe or primer. Among these techniques, the DNA chip method is a detection technique which is particularly attracting attention. A large number of similar nucleotide sequences can be arranged in minute compartments on a DNA chip. By controlling the reaction environment of the fine spaces on the DNA chip, the presence or absence of hybridization based on slight differences of the nucleotide sequences can be detected. However, the reproducibility of analyzed data obtained using DNA chip is a major problem. The hybridization conditions on the DNA chip must be precisely set, due to the fine reaction spaces. In order to maintain a fixed level of reproducibility, sophisticated techniques and utmost caution are required. Moreover, since it is a PCR dependent technique, two steps are required; the high price of a DNA chip is a further problem that needs to be resolved.

On the other hand, the Invader method (Mol. Diagn. 4: p. 135, 1999) and the RCA method (Nat. Genet. 19: p. 225, 1998) have been reported as examples of PCR-independent mutation detection techniques. However, the reaction specificity is dependent on the probe set of two adjacent regions for both of these methods. As was pointed out with respect to PCR, it is difficult to simultaneously identify similar genes and detect mutations with only two regions.

As has been described above, known methods for confirming nucleotide sequences have problems. For example, accurate identification of slight nucleotide sequences cannot be performed in a single step. Also, the methods encounter difficulty in simultaneously-identifying similar genes and detecting mutations. Further, even if it is technically possible to identify similar genes and detect mutations, as with PCR-dependent technology, it is either difficult to maintain accuracy or a complex procedure is required, due to the need for a plurality of steps. Finally, improvement in economic aspects is desired as well.

DISCLOSURE OF THE INVENTION

An object of the present invention is to provide a novel reaction principle which simultaneously enables the identification of similar genes and the accurate detection of slight differences in nucleotide sequences. More specifically, the object of the present invention is to provide methods that allow detection of mutations and polymorphisms in a target nucleotide sequence by a nucleic acid synthesis method, wherein the nucleotide sequence in the target nucleotide sequence can be repeatedly checked.

The present inventors focused on the fact that a majority of primers do not hybridize with the target nucleotide sequence, which is a problem in methods for confirming nucleotide sequence based on known nucleic acid amplification reactions. Specifically, a nucleotide sequence originating from a primer is directly used as a template for complementary strand synthesis in the PCR method. Thus, the mechanism for checking the target nucleotide sequence by primer hybridization in fact acts for only an extremely small portion of the overall reaction. The majority of the reaction proceeds by hybridization of the primer to the complementary strand that has simply copied the nucleotide sequence of the primer. Such a system is far from checking the target nucleotide sequence.

Therefore, the inventors contemplated that slight differences in a target nucleotide sequence could be accurately detected by utilizing a nucleic acid synthesis reaction which contains numerous steps of hybridization to the nucleotide sequence of the target nucleotide sequence. Then, the inventors discovered that a more precise checking mechanism for the target nucleotide sequence could be achieved by utilizing a 3'-end, at which complementary strand synthesis has been completed, as the origin of the next complementary strand synthesis, and completed the present invention.

More specifically, a primer for nucleotide sequence identification was provided for the first time by complementary strand synthesis, and the inventors discovered that a sophisticated checking mechanism could be realized, based on the nucleic acid synthesis method wherein the primer acts as the origin of complementary strand synthesis that uses itself as the template. This type of nucleic acid synthesis reaction has been already reported by the inventors of the present invention (Nucleic Acid Res. 2000, Vol. 28, No. 12, e63, WO 00/28082). The present invention solved the above noted problems based on this nucleic acid synthesis method. More specifically, the present invention relates to methods for detecting mutations and/or polymorphisms, as well as reagent kits used therefore as follows:

[1] a method for detecting mutations and/or polymorphisms within a specific region of a target nucleotide sequence comprising the steps of: (1) incubating the following elements (a) to (e) under conditions that allow complementary strand synthesis, wherein second and first primers are used as origins; and (2) correlating the amount of the product synthesized by the complementary strand synthesis reaction, which uses the target nucleotide sequence as the template, with the presence of a mutation and/or polymorphism in the specific region, wherein the nucleotide sequence arranged on at least one of the 5'-ends of the second and first primer contains a nucleotide sequence that is complementary to the predicted nucleotide sequence of said specific region or the complementary strand thereof, and wherein the complementary strand, that is synthesized using the nucleotide sequence arranged on the 5'-end as the template and functions as the origin of complementary strand synthesis by annealing to the specific region or the complementary strand thereof, inhibits the complementary strand synthesis when the nucleotide sequence that contains the specific region is not a predicted one:

(a) nucleic acid sample comprising a target nucleotide sequence;

(b) DNA polymerase catalyzing complementary strand synthesis which includes strand displacement;

(c) second primer, wherein the 3'-end of the second primer anneals to the 3'-side region of one of said target nucleotide sequence strands, and the 5'-side of the second primer includes a nucleotide sequence complementary to the predicted nucleotide sequence that constitutes a region on the products of the complementary strand synthesis reaction that uses the primer as the origin;

(d) first primer, wherein the 3'-end of the first primer anneals to the 3'-side region of the other said target nucleotide sequence strand, and the 5'-side of the first primer includes a nucleotide sequence complementary to the predicted nucleotide sequence that constitutes a region on the products of the complementary strand synthesis reaction that uses the primer as the origin; and (e) nucleotide substrates;

[2] the method of [1], wherein both of the nucleotide sequences arranged on the 5'-end of the second primer or first primer contain a nucleotide sequence that is complementary to the predicted nucleotide sequence of said specific region or the complementary strand thereof, and wherein the complementary strand, that is synthesized using the nucleotide sequence arranged on the 5'-end as the template and functions as the origin of complementary strand synthesis by annealing to the specific region or the complementary strand thereof, inhibits the complementary strand synthesis when the nucleotide sequence that contains the specific region is not a predicted one;

[3] the method of [1], additionally comprising the following elements:

(1) third primer, wherein the third primer serves as the origin of the complementary strand synthesis reaction wherein the 3'-side of the annealing region of the first primer on the template functions as the origin; and, (2) fourth primer, wherein the fourth primer serves as the origin of the complementary strand synthesis reaction wherein the 3'-side of the annealing region of the second primer on the template functions as the origin;

[4] the method of [1], wherein a gene comprising a nucleotide sequence similar to the nucleotide sequence of the target nucleotide sequence is present in the same sample;

[5] the method of [4], wherein a gene comprising a nucleotide sequence similar to the nucleotide sequence of the target nucleotide sequence is a family gene and/or a pseudogene;

[6] the method of [5], wherein the family gene and/or the pseudogene is any gene selected from the group consisting of the cytochrome P450 family, human leukocyte histocompatibility antigens, and platelet alloantigens;

[7] the method of [1], wherein the polymorphism is a single nucleotide polymorphism;

[8] the method of [1], wherein the target nucleotide sequence is selected from the nucleotide sequences of genes from any pathogenic virus or pathogenic microorganism selected from the group consisting of hepatitis C virus, influenza virus, malaria, and *Helicobacter pylori*;

[9] the method of [1], wherein the incubation is performed in the presence of a melting temperature regulator;

[10] the method of [9], wherein the melting temperature regulator is at least one of the compounds selected from the group of betaine, proline, and dimethylsulfoxide;

[11] the method of [1], wherein the nucleic acid sample is double stranded;

[12] the method of [1], wherein the method is carried out in the presence of a nucleic acid detector to detect the presence of a mutation and/or polymorphism based on a change in the signal of the detector;

[13] the method of [1], wherein a nucleotide sequence derived from the same organism as the organism for which a mutation and/or polymorphism is to be detected, and which sequence is confessed to include no mutation and/or polymorphism, is used as an internal standard, and the presence of a mutation and/or polymorphism is detected by comparing the amounts of synthesized products obtained using the nucleotide sequences as templates;

[14] the method of [1], additionally comprising:

(f) first loop primer, wherein the first loop primer provides a origin for complementary strand synthesis between a region originating from the first primer in the elongation product of the first primer and said arbitrary region for the first primer; and/or (g) second loop primer, wherein the second loop primer provides a origin for complementary strand synthesis between a region originating from the second primer in the elongation product of the second primer and said arbitrary region for the second primer;

[15] the method of [1], when the nucleotide sequence that contains said specific region is not the predicted nucleotide sequence, a mismatch occurs during annealing to the specific region or the complementary strand thereof in the second to the fourth nucleotide from the 3'-end of the complementary strand which is synthesized using the nucleotide sequence arranged on the 5'-end of the first primer and/or second primer as the template;

[16] a kit comprising the following elements for detecting a mutation and/or polymorphism of a specific region in a target nucleotide sequence, wherein a nucleotide sequence arranged on at least one of the 5'-ends of a second and first primer contains a nucleotide sequence complementary to the predicted nucleotide sequence of said specific region or the complementary strand-thereof, wherein the complementary strand, that is synthesized using the nucleotide sequence arranged on this 5'-end as the template and functions as the origin of complementary strand synthesis by annealing to the specific region or the complementary strand thereof, inhibits the complementary strand synthesis and when the nucleotide sequence that contains the specific region is not a predicted one:

i) second primer, wherein the 3'-end of the second primer anneals to the 3'-side region of one of said target nucleotide sequence strands, and the 5'-side of the second primer includes a nucleotide sequence complementary to the predicted nucleotide sequence that constitutes a region on the product of the complementary strand synthesis reaction that uses this primer as the origin;

ii) first primer, wherein the 3'-end of the first primer anneals to the 3'-side region of the other said target nucleotide sequence strand, and the 5'-side of the first primer includes a nucleotide sequence complementary to the predicted nucleotide sequence that contains a region on the product of the complementary strand synthesis reaction that uses the primer as the origin;

iii) DNA polymerase catalyzing complementary strand synthesis which includes a strand displacement; and iv) nucleotide substrates;

[17] the kit of [16] additionally comprising the following elements:

v) third primer which serves as the origin of the complementary strand synthesis by annealing to the 3'-side of the first primer annealing region in the template; and vi) fourth primer which serves as the origin of the complementary strand synthesis by annealing to the 3'-side of the second primer annealing region in the template;

[18] the kit of [16] additionally comprising the elements of:

vii) fifth primer amplifying an internal standard, wherein the 3'-end of the fifth primer anneals to the 3'-side region of one of the target nucleotide sequence strands of an internal standard, and the 5'-side of the fifth primer includes a nucleotide sequence complementary to a nucleotide sequence that contains an arbitrary region of a product of the complementary strand synthesis reaction that uses the primer as the origin; and iix) sixth primer amplifying an internal standard, wherein the 3'-end of the sixth primer anneals to the 3'-side region of one of the target nucleotide sequence strands of an internal standard, and the 5'-side of the sixth primer includes a nucleotide sequence complementary to the nucleotide sequence that contains a region of a product of the complementary strand synthesis reaction that uses the primer as the origin;

[19] the kit of [18] additionally comprising the elements of:

ix) seventh primer that serves as the origin of the complementary strand synthesis by annealing to the 3'-side of the sixth primer annealing region in the template; and x) eighth primer that serves as the origin of the complementary strand synthesis by annealing to the 3'-side of the sixth primer annealing region in the template;

[20] a method for detecting mutations and/or polymorphisms in a specific region of a target nucleotide sequence, wherein the nucleotide sequence arranged on at least one of the 5'-ends of a second and first primer contains a nucleotide sequence that is complementary to the predicted nucleotide sequence of said specific region or the complementary strand thereof, and wherein the complementary strand, that is synthesized using the nucleotide sequence arranged on the 5'-end as the template and functions as the origin of complementary strand synthesis by annealing to the specific region or the complementary strand thereof, inhibits the complementary strand synthesis when the nucleotide sequence that contains the specific region is not a predicted one, which method comprises the steps of:

a) annealing a first primer to a target nucleotide sequence to carry out a complementary strand synthesis reaction using the primer as the origin, wherein the 3'-end of the first primer anneals to a 3'-side region of one of said target nucleotide sequence strands, and the 5'-side of the first primer includes a nucleotide sequence complementary to the predicted nucleotide sequence that contains a region on the product of the complementary strand synthesis reaction that uses the primer as the origin;

b) putting the region, to be annealed with the second primer, in the elongation product of the first primer synthesized in step a) into a state allowing base pairing of the region to the second primer, annealing them to synthesize the complementary strand using the elongation product of the first primer as a template; wherein the 3'-end of the second primer anneals to the 3'-side region of the other said target nucleotide sequence strand, and the 5'-side of the second primer includes a nucleotide sequence complementary to the predicted nucleotide sequence that contains a region on the product of the complementary strand synthesis reaction that uses the primer as the origin;

c) carrying out a complementary strand synthesis, using the elongation product of the second primer itself as a template, by annealing the 3'-end of the product with said predicted nucleotide sequence to the first primer in said elongation product;

d) carrying out a complementary strand synthesis using the complementary strand synthesized in step c) itself as a template by annealing the 3'-end of the complementary strand synthesized in step c) with said predicted nucleotide sequence to the second primer in said elongation product; and e) correlating the amount of synthesized product obtained using the second primer as the origin with the presence of a mutation and/or polymorphism in the specific region;

[21] the method of [20], wherein step b) comprises a step of converting the elongation product of the first primer to a single strand by displacement, which displacement is conducted by a complementary strand synthesis reaction using the third primer that uses the 3'-side of the region annealing to the first primer in the template as the origin;

[22] the method of [20], wherein step c) comprises a step of converting the elongation product of the second primer to a single strand by displacement, which displacement is conducted by a complementary strand synthesis reaction using the fourth primer that uses the 3'-side of the region annealing to the second primer in the template as the origin;

[23] the method of [20], wherein the nucleotide sequence arranged on at least one of the 5'-ends of the second and first primer contains a nucleotide sequence that is complementary to the predicted nucleotide sequence of said specific region or to the complementary strand thereof, and wherein the complementary strand, that is synthesized using the nucleotide sequence arranged on the 5'-end as the template and functions as the origin of complementary strand synthesis by annealing to a specific region or the complementary strand thereof, inhibits the complementary strand synthesis when the nucleotide sequence that contains the specific region is not a predicted one, which method additionally comprises the steps of:

1) carrying out the complementary strand synthesis reaction of step (c) in the method of [20] by forming a loop forming region, that forms a base pair with a nucleotide sequence complementary to the 3'-end of the first primer, by annealing the 3'-end and the predicted nucleotide sequence within the elongation product of the second primer, and using the 3'-end of itself as the origin for the complementary strand synthesis;

2) annealing the first primer to the loop forming region, and carrying out complementary strand synthesis using the first primer as the origin with DNA polymerase catalyzing complementary strand synthesis which includes a strand displacement;

3) displacing the product elongated from its own 3'-end by a complementary strand synthesis reaction using a primer, that anneals to the loop forming region as the origin, to enable base pairing of the 3'-end and said predicted nucleotide sequence again;

4) forming a single stranded nucleic acid by displacing the complementary strand synthesized using the loop forming region as the origin by annealing the 3'-end, that was put in a state to form a base pair in step 3), to said predicted nucleotide sequence as the origin of the complementary strand synthesis to carry out a complementary strand synthesis reaction which uses itself as the template;

5) forming a loop forming region, that forms a base pair with a nucleotide sequence complementary to the 3'-end of the second primer, by annealing the 3'-end and said predicted nucleotide sequence for the second primer, and by complementary strand synthesis;

6) annealing the second primer to the loop forming region, and carrying out a complementary strand synthesis using the second primer as the origin by DNA polymerase catalyzing complementary strand synthesis including a strand displacement;

7) repeating steps 3) to 6); and 8) following step 7) and/or in parallel with step 7) detecting the formation of a single stranded nucleic acid, in which the target nucleotide sequence and the complementary strand thereof are repeatedly linked, and correlating the amount of formed nucleic acids with a mutation and/or polymorphism;

[24] the method of [23], additionally comprising the steps of:

9) carrying out the complementary strand synthesis reaction using the single stranded nucleic acid formed in step 4) as the template by annealing the 3'-end thereof to said predicted nucleotide sequence for the second primer, forming a loop forming region, that forms a base pair with a nucleotide sequence complementary to the 3'-end of the second primer, and using the 3'-end of itself as the origin for the complementary strand synthesis;

10) annealing the second primer to the loop forming region, which region was formed by annealing the 3'-end with its own said specific region, and carrying out complementary strand synthesis using the second primer as the origin by DNA polymerase catalyzing complementary strand synthesis which includes a strand displacement;

11) displacing the product elongated from its own 3'-end by a complementary strand synthesis reaction using a primer, that anneals to the loop forming region as the origin, to enable base pairing of the 3'-end and said predicted nucleotide sequence again;

12) forming a single stranded nucleic acid by displacing the complementary strand synthesized using the loop forming region as the origin by annealing the 3'-end, that was put in a state to form a base pair in step 11), to said predicted nucleotide sequence as the origin of complementary strand synthesis to carry out a complementary strand synthesis reaction which uses itself as the template;

13) forming a loop forming region, that forms a base pair with a nucleotide sequence complementary to the 3'-end of the first primer, by annealing of the 3'-end and said predicted nucleotide sequence and carrying out-complementary strand synthesis;

14) annealing the first primer to the loop forming region, and carrying out a complementary strand synthesis using the first primer as the origin by DNA polymerase catalyzing complementary strand synthesis which includes strand displacement;

15) repeating steps 11) to 14); and 16) following step 15) and/or in parallel with step 15) detecting the formation of a single stranded nucleic acid, in which the target nucleotide sequence and the complementary strand thereof are repeatedly linked, and correlating the amount of formed nucleic acids with a mutation and/or polymorphism;

[25] the method of [24], additionally comprising the step of:

17) forming a loop forming region, that forms a base pair with a nucleotide sequence complementary to the 3'-end of the first primer, by annealing the 3'-end of the single stranded nucleic acid formed in step 12) with said predicted nucleic acid sequence on itself, and carrying out a complementary strand synthesis reaction using the 3'-end of itself as the origin and itself as the template; and

[26] the method of [20], wherein the nucleotide sequence arranged on the 5'-end of both of the second primer and first primer contains a nucleotide sequence complementary to the predicted nucleotide sequence of said specific region or the complementary strand thereof, and wherein the complementary strand, that is synthesized using the nucleotide sequence arranged on the 5'-end as the template and functions as the origin of complementary strand synthesis by annealing to the specific region or the complementary strand thereof, inhibits the complementary strand synthesis when the nucleotide sequence that contains the specific region is not a predicted one.

[Definition of Terms]

The following terms used in the present invention have respective meanings indicated below.

Mutation: Herein, "mutation" refers to a difference in the nucleotide sequence of a nucleic acid that is observed among individual organisms (including viruses) of the same origin. With respect to multicellular organisms, differences observed among organs, cells, and so on within an individual are also included as mutations. Mutations arise from point mutations, deletions, insertions, duplications, inversions, and translocations. Further, mutations may occur within gene regions (protein coding regions and intron sequences) or in expression regulatory regions, such as promoters and enhancers. Differences in nucleotide sequences found in other genomic sequences are also included in mutations.

Polymorphism: Among the above mutations, those that are present at a frequency of 1% or more within a certain population are particularly referred to as "polymorphisms". Among polymorphisms, polymorphisms consisting of displacement, insertion, or deletion of a single nucleotide are particularly referred to as single nucleic polymorphisms (or "SNPs").

Target nucleotide sequence: A "target nucleotide sequence" is a nucleotide sequence that contains one or more mutations or polymorphisms to be detected, and which comprises a region wherein the 3'-side is determined by a primer. Hereinafter, both of the expressions "5'-side" and "3'-side" refer to a direction in the strand which serves as the template. More specifically, a nucleotide sequence surrounded by regions, that anneal with the primers of the present invention, comprises the target nucleotide sequence of the present invention. In general, the nucleotide sequence of a nucleic acid is described from the 5'-side to the 3'-side of the sense strand. Further, the target nucleotide sequence of the present invention includes not only the sense strand but also the nucleotide sequence of the complementary strand thereof, i.e. the antisense strand. More specifically, the term "target nucleotide sequence" refers to at least to either of the nucleotide sequence to be synthesized or the complementary strand thereof. The target nucleotide sequence contains a specific region described below.

Specific region: A "specific region" is a region contained in the above target nucleotide sequence and which includes the one or more mutations or polymorphisms to be detected. According to the detection method of the present invention, a complementary strand, to which a complementary strand to the nucleotide sequence predicted in the specific region is attached to the 5'-end, is synthesized. Further, the nucleotide sequence complementary to the specific region must be added so as to comprise the 5'-end of the synthesized complementary strand.

Predicted nucleotide sequence: A "predicted nucleotide sequence" can be either a wild type nucleotide sequence or a nucleotide sequence containing specific mutation(s). When a wild type nucleotide sequence is used as the predicted nucleotide sequence, the presence or absence of the wild type nucleotide sequence in the target nucleotide sequence is detected, while the presence or absence of a nucleotide sequence containing specific mutations or polymorphisms is detected in the target nucleotide sequence by the nucleotide sequence of a specific mutation or polymorphism.

3'-end or 5'-end: The terms "3'-end" and "5'-end" do not refer to the nucleotide of either terminus, but rather, refer to a region located at the terminus that includes the single terminal nucleotide. More specifically, 500 nucleotides, preferably 100 nucleotides, or at least 20 nucleotides from either terminus are included in the terms "3'-end" and "5'-end". In contrast, in order to indicate a single terminal nucleotide or a nucleotide at a specific location present in the vicinity of a terminus, the numerical value of the location thereof is specified.

Template and complementary strand: The term "template" as used in the present invention refers to nucleic acids that serves as a template in complementary strand synthesis. Although a complementary strand having a nucleotide sequence that is complementary to a template is a strand corresponding to the template, the relationship between the two is merely relative. Specifically, a strand synthesized as a complementary strand has the ability to function as a template. In other words, a complementary strand can also serve as a template.

Nucleic acid synthesis and amplification: Nucleic acid synthesis herein refers to the elongation of nucleic acids from an oligonucleotide which serves as the synthesis origin. A series of reactions including the continuous reaction of formation of other nucleic acids and elongation of the formed nucleic acids in addition to synthesis are collectively referred to as "amplification".

Annealing: The terms "annealing" and "hybridization" refer to the formation of a double helix structure of nucleic acids by base pairing based on the Watson-Crick model. Thus, even if a base pairing of a nucleic acid strand is composed of a single strand, the forming of a base pair by the complementary nucleotide sequences within a molecule is considered as annealing or hybridization. According to the present invention, annealing and hybridization are synonymous at the point that nucleic acids form a double helix structure due to base pairing. When the 3'-end of the nucleic acid forming a base pair serves as the origin of complementary strand synthesis, it is particularly referred to as annealing. However, this does not mean that a base pair formed by hybridization does not serve as an origin of complementary strand synthesis.

Substantially identical nucleotide sequence: A sequence is deemed "substantially identical" to the target sequence when a complementary strand, that is synthesized using the sequence as a template, anneals to the target sequence and serves as the origin of complementary strand synthesis. The terms "identical" and "complementary" as used herein encompass cases that are not completely identical and not completely complementary. More specifically, an sequence identical to a certain sequence also includes a sequence complementary to a nucleotide sequence that can anneal to the certain sequence. On the other hand, a complementary sequence refers to a sequence that anneals under stringent conditions, and provides a 3'-end as the origin for complementary strand synthesis. More specifically, a nucleotide sequence that has an identity of typically 50% to 100%, normally 70% to 100%, and preferably 80% to 100% to a certain nucleotide sequence is mentioned as a sequence that is substantially identical. Identity can be determined based on known algorithms such as BLAST.

[Description of the Principle]

A nucleotide sequence in a specific region of a target nucleotide sequence is checked based on the principle as described below in the method for detecting mutations and polymorphisms of the present invention. First, the following second primer and first primer are used in the present invention. Each of the second primer and first primer used in the present invention comprises at the 3'-end thereof, a nucleotide sequence that anneals to the 3'-side of a target nucleotide sequence, and, at the 5'-end thereof, a nucleotide sequence that is complementary to an arbitrary region in the product elongated using the 3'-end of the primers as the origin. At least one of the nucleotide sequences arranged at the 5'-end of the primers is designed so as to include a nucleotide sequence complementary to the predicted nucleotide sequence of said specific region or the complementary strand thereof. The nucleotide sequence of the complementary strand synthesized using the nucleotide sequence arranged on the 5'-end of the primer as the template is checked utilizing the inhibition of the complementary strand synthesis when the nucleotide sequence of the specific region is not the predicted one. The checking mechanism always works when the 3'-end anneals to the specific region (or the complementary strand thereof) and serves as the complementary strand synthesis origin. Thus, any difference appearing in a nucleotide sequence in the specific region can be detected clearly as a difference in the amount of reaction product.

To actually detect mutations and/or polymorphisms based on the reaction principle described above, for example, the following reaction can be used. Specifically, the present invention relates to a method for detecting mutations and/or polymorphisms in a specific region of a target nucleotide sequence, wherein the nucleotide sequence arranged on at least one of the 5'-ends of the second primer and first primer contains a nucleotide sequence that is complementary to the predicted nucleotide sequence of above-mentioned specific region or the complementary stand thereof, and wherein the complementary strand, that is synthesized using the nucleotide sequence arranged on the 5'-end as the template and functions as the origin of the complementary strand synthesis by annealing to the specific region or the complementary strand thereof, inhibits the complementary strand synthesis when the nucleotide sequence that contains the specific region is not a predicted one, which method comprises the steps of:

(a) annealing the first primer to a target nucleotide sequence to carry out complementary strand synthesis using the primer as the origin, wherein the 3'-end of the first-primer anneals to a 3'-side region of one of said two target nucleotide sequence strands, and the 5'-side of the first primer includes a nucleotide sequence that comprises a region on the products of the complementary strand synthesis that uses this primer as the origin;

(b) putting the region, to be annealed with the second primer, in the elongation products of the first primer synthesized in the step (a) into a state allowing base pairing of the region to the second primer, annealing them to synthesize the complementary strand using the elongation product of the first primer as a template, wherein the 3'-end of the second primer anneals to the 3'-side region of the other said target nucleotide sequence strand, and the 5'-side of the second primer includes a nucleotide sequence complementary to the predicted nucleotide sequence that comprises a region on the products of the complementary strand synthesis that uses the primer as the origin;

(c) carrying out complementary strand synthesis using the elongation product of the second primer itself as a template by annealing the 3'-end of the products with said predicted nucleotide sequence to the first primer in said elongation products;

(d) carrying out complementary strand synthesis using the complementary strand synthesized in step c) itself as a template by annealing the 3'-end of the complementary strand synthesized in step (c) with said predicted nucleotide sequence to the second primer in said elongation products; and (e) correlating the amount of synthesized products obtained using the second primer as the origin with the presence of mutations and/or polymorphisms in the specific region.

In the present invention, the 3'-ends of the products elongated from the second primer and/or first primer anneal to the specific region on itself, and serve as origin of the complementary strand synthesis using the elongation products themselves as the templates. In this reaction, when the nucleotide sequence of the specific region is the predicted one, the complementary strand synthesis proceeds, using the 3'-end as the origin. On the contrary, when the nucleotide sequence is not the predicted one, the 3'-end cannot serve as the complementary strand synthesis origin, and as a result the complementary strand synthesis is inhibited. Thus, the specific region can be determined whether it has a predicted nucleotide sequence or not, using products of the complementary strand synthesis as an index, in which synthesis the 3'-end is used as the primer and the products themselves as the templates.

The complementary strand synthesized in this step extends to its own 5'-end to complete the extension. According to the present invention, the 5'-end of the template always contains a nucleotide sequence corresponding to that arranged on the 5'-end of the primer. That is, a nucleotide sequence complementary to an arbitrary region in the elongation products is added to the 5'-end of the template. Thus, a nucleotide sequence annealing to the arbitrary region is reproduced on the 3'-end of the complementary strand synthesized using the elongation product as the template. Then, complementary strand synthesis starts again when the 3'-end and the arbitrary region, to which the 3'-end anneals, forms a base pair by certain means.

According to the present invention, a nucleotide sequence complementary to a specific region on an elongation product (or the complementary strand thereof), which product is synthesized using the 3'-end of at least either of the second and first primers as the origin, is arranged on the 5'-end thereof. Hereinafter, a second or first primer containing the nucleotide sequence complementary to a specific region (or the complementary strand thereof) on the 5'-end is particularly referred to as the checking primer in some cases.

Thus, the 3'-end of the elongation products, synthesized using the 5'-end of the checking primer as the template, checks the nucleotide sequence of the specific region (or the complementary strand thereof) every time it anneals to the specific region (or the complementary strand thereof). Thus, resumption of the complementary strand synthesis depends on whether the specific region contains the predicted nucleotide sequence or not. As is obvious from the above description, an important characteristic of the present invention is that the reaction of complementary strand synthesis, which proceeds using itself as the template, proceeds while the nucleotide sequence in the specific region is checked over and over again. Thus, even if a wrong product is generated in the complementary strand synthesis, the mechanism for checking errors in nucleotide sequences works in the next round of complementary strand synthesis, wherein the product is used as a template. As a result, complementary strand synthesis using the wrong product is inhibited in the subsequent round, and thus, "noises" resulting from erroneous synthesis of a complementary strand can be dramatically reduced according to the present invention.

The reaction as described above, to actually detect mutations and/or polymorphisms based on the principle of the present invention, can be performed by merely incubating the following components under appropriate conditions. More specifically, the present invention is a method for detecting mutations and/or polymorphisms using a check primer as at least one of a second primer or first primer comprising the steps of: incubating the following components (a) to (e) under conditions allowing complementary strand synthesis using the second and first primers as the origins; and correlating the amount of reaction products of the complementary strand synthesis using a target nucleotide sequence as the template to the presence of mutations and/or polymorphisms in the specific region:

(a) nucleic acid sample comprising a target nucleotide sequence;

(b) DNA polymerase catalyzing complementary strand synthesis which includes strand displacement;

(c) second primer: the 3'-end of the second primer anneals to the 3-side region of one of said target nucleotide sequence strands, and the 5'-side of the second primer contains a nucleotide sequence complementary to the predicted nucleotide sequence that constitutes a region on the products of complementary strand synthesis that uses the primer as the origin;

(d) first primer: the 3'-end of the first primer anneals to the 3'-side region of the other said target nucleotide sequence strand, and the 5'-side of the first primer contains a nucleotide sequence complementary to the predicted nucleotide sequence that constitutes a region on the products of the complementary strand synthesis that uses the primer as the origin;

(e) nucleotide substrates.

The nucleic acid-amplification method using the second and first primers is the "LAMP method" previously reported by the present inventors (Nucleic Acid Res. 2000 Vol. 28, No. 12 e63; WO 00/28082). However, it is indeed a novel finding provided by the present invention that a highly accurate checking mechanism for nucleotide sequences is provided by the use of at least one of the primers, utilized in the LAMP method, as a checking primer in the method for detecting mutations and polymorphisms.

A first primer, used in a reaction as described above, comprises regions as follows:

X2: a region containing a nucleotide sequence complementary to X2c, which region determines the 3'-side of the target nucleotide sequence; and X1c: a region located on the 5'-side of X2c mentioned above, and containing a nucleotide sequence complementary to the nucleotide sequence predicted in the region X1 which exists on the products elongated from the first primer. X1 is a sequence of an arbitrary region on the elongation product of the first primer, which arbitrary region is located between the 3'-end of the first primer and the specific nucleotide sequence. X1c also includes regions having substantially the same nucleotide sequence as that predicted for the arbitrary region X1c.

The principle of the reaction in the LAMP method and the application of the method to the present invention are described below with reference to FIGS. 1 to 4. In the description below, FA refers to the first primer and RA to the second primer. FA consists of F2 and F1c, corresponding to the above-mentioned X2 and X1c, respectively. The F1c comprised in FA also contains those with a nucleotide sequence substantially the same as that of F1c. According to the present invention, for example, an arbitrarily selected region, such as F1 above, can anneal to a polynucleotide containing a nucleotide sequence complementary to the region, and so long as a complementary strand synthesized using the polynucleotide as the synthesis origin has the function required for the present invention the region can be selected from any arbitrary regions.

On the other hand, a primer consisting of R2 and R1c, corresponding to the above X2 and X1c, respectively, can be used as the second primer, RA, of the present invention. In this case, for example, when RA is used as the checking primer, R1c comprises the nucleotide sequence predicted for the specific region R1c containing mutations and/or polymorphisms to be detected in the elongation products from FA, and R2 comprises the nucleotide sequence complementary to the nucleotide sequence R2c, which constitutes the arbitrary region in the elongation products from FA.

When using the checking primer, RA, for the detection method of the present invention, FA can be also used as the other checking primer. During the reaction of complementary strand synthesis by the checking primer RA as described below, the 3'-end of elongation products from FA is always ready for base pairing, and thus, repeats the complementary strand synthesis reaction using the products themselves as the template. On the other hand, the elongation products from RA are also continuously generated as single strands. Further, like those from FA, the elongation products from RA also serve themselves as the template for complementary strand synthesis, due to its 3'-end. The checking mechanism for the nucleotide sequence of the elongation products from FA can be provided through use of a checking primer for FA in this reaction cycling. The checking mechanism provided for the nucleotide sequence in the specific region in complementary strand synthesis by the use of FA in the present invention proceeds according to the same principle as the nucleotide sequence-checking mechanism by the RA described above. Namely, the same principle is employed for a complementary strand of a specific region.

The reaction, in which checking primers are used as both of FA and RA, is described below in more detail. The complementary strand synthesis using R1 as the origin [FIG. 4-(9)] is inhibited when a checking primer is employed as RA. Likewise, the complementary strand synthesis using F1 as the origin [FIG. 3-(8)] is inhibited when a checking primer is employed as FA. However, detection of minor differences in nucleotide sequences utilizing the specificity of polynucleotide annealing is practically impossible as it has been for PCR. The same is also true for the reaction of the present invention. Even if the complementary strand synthesis is inhibited in the present invention when the specific region contains no predicted nucleotide sequence, it is realistic to assume that the reaction cannot be completely inhibited.

The case of complementary strand synthesis wherein the synthesis is not inhibited despite the fact that the specific region is not a predicted nucleotide sequence is discussed below. In FIGS. 1 to 4, F1 and R1c (or R1 and F1c) are separately illustrated. The reaction illustrated in these Figures represent reactions using a checking primer as either FA or RA.

On the other hand, when checking primers are used as both FA and RA, a nucleotide sequence, that is complementary to a specific region, anneals to the strand from both directions. Accordingly, at least a part of R1c, to which R1 anneals, overlaps with F1. Simultaneously, at least a part of F1c, which is the complementary strand of F1, overlaps with R1.

First, a complementary strand synthesis reaction using F1 as the origin [FIG. 3-(8)], a reaction with an erroneous complementary strand synthesis, is discussed below. As the first step, R1 anneals to a specific region of an erroneously synthesized elongation product, and then, a complementary strand is synthesized. A checking primer is provided as RA, and the 3'-end R1, that is synthesized using RA as the template anneals to a region comprising the region which was originally the 3-end of FA. Namely, the region comprises the predicted nucleotide sequence to proceed the complementary strand synthesis without the checking function. However, when the complementary strand is synthesized to the 5'-end, the 3'-end thereof is a complementary strand to the 5'-end of the checking primer FA. Thus, the checking mechanism functions by annealing the 3'-end of the synthesized complementary strand to the specific region.

As described above, there are cases where the checking mechanism for RA does not function when the checking mechanism for FA functions in a reaction wherein checking primers are adopted as both FA and RA. However, the actual probability that RA and FA react in the order as indicated in FIGS. 1 to 4 is theoretically ½, when the target nucleotide sequence is a double-stranded nucleic acid. The remaining half of the reactions proceed in an order contrasting to that in FIGS. 1 to 4. More specifically, "R" must be read as "F" in FIGS. 1 to 4 to explain the remaining half of the reaction, because RA and FA respectively anneal to the two strands constituting the target nucleotide sequence and the subsequent reaction proceeds in the same manner.

Alternatively, in explaining the reaction of the present invention based on FIGS. 1 to 4, one can also state that RA (or FA) does not represent a specific primer annealing to either of the strands of the target nucleotide sequence. Namely, for the convenience of explanation, the Figures only explain the first annealed primer as RA.

Accordingly, one can readily recognize the significance of the checking primer as not only FA but also RA. Specifically, since a similar checking mechanism as that for the complementary strand of FA as described above works on the complementary strand of RA, the more checking mechanism in the whole reaction system functions in total. Thus, the use of checking primers as both FA and RA is a preferred embodiment of the present invention.

The checking mechanism based on the present invention is discussed in more detail below. In spite of using checking primers as both FA and RA in the present invention, it is theoretically true that there are some reactions wherein the checking mechanism of the present invention does not work. Specifically, the 3'-end of an product elongated from a primer annealed to the loop portion adjacent to the region containing a nucleotide sequence originating from the 5'-end of the checking primer anneals not to the specific region but to the nucleotide sequence originating from either of the primers. The checking mechanism does not work when the 3'-end anneals not to the specific region but to the nucleotide sequence originating from the primer. However, according to the present invention, it is important that the checking mechanism functions many times until such a product, on which the checking mechanism does not work, is produced.

Probability X where a product on which a checking mechanism does not function is produced is represented as $A^n$. Herein, A is the probability where the reaction proceeds, despite the specific region does not include the predicted nucleotide sequence; and n is the number of counts of the checking mechanism that worked prior to the generation of the product on which the checking mechanism has not worked. For example, even in the case where reaction products are generated without the checking mechanism at a rate of 5%, probability X is only $0.05^3=0.000125$ (0.01%) if the checking mechanism works 3 times. Namely, the risk can be reduced to about 1/500 compared to a case where the checking mechanism works only once. Thus, it is obvious that the probability generating the product, on which the checking mechanism has not worked, is markedly reduced in the present invention as compared with that in the reaction where the checking mechanism works only once.

The above-mentioned target nucleotide sequence is a part or the whole of a detection subject or a nucleic acid derived from the detection subject. The target nucleotide sequence may be a single-stranded or double-stranded sequence. When it is a double-stranded nucleic acid, at least a part of the nucleotide sequences of the 3'-ends of respective strands that determine the target nucleotide sequence and the specific region within the target nucleotide sequence is already known or are predictable. Alternatively, when the target nucleotide sequence is a single-stranded nucleic acid, at least a part of the nucleotide sequences that determines the 3'-side of the target nucleotide sequence, the nucleotide sequence of the 3'-side of the complementary strand, and that of the specific region within the target nucleotide sequence is already known or are predictable. The nucleotide sequence of the above-mentioned 3'end X2c and the specific region X1c located on the 5'-side thereof are regions which nucleotide sequences should be determined. The specific region of the present invention comprises nucleotides which are potentially mutated and/or contain one or more polymorphisms. The checking primer of the present invention should be designed so that the complementary strand synthesis is inhibited when the nucleotide in the specific region, which nucleotide is potentially mutated and/or have polymorphism, differ from the predicted nucleotide.

The checking primer of the present invention can be designed, for example, as follows. Specifically, when a complementary strand is synthesized using the checking primer as the template, the primer is designed so that the adjacent region to the 3'-end of the synthesized complementary strand corresponds to the site complementary to the nucleotide residue, which is potentially mutated and/or have polymorphism. The complementary strand synthesis reaction of a nucleic acid is markedly inhibited when mismatches exist at the 3'-end, that serves as the complementary strand synthesis origin, or in adjacent regions thereto. More specifically, the reaction of complementary strand synthesis is markedly inhibited when there are mismatches within a region 10 bases from the 3'-end, which serves as the complementary strand synthesis origin, particularly preferably 2 to 4 bases counted from the 3'-end, more preferably a mismatch of the 2nd or the 3rd nucleotide. Thus, it is preferable to design the 5'-side nucleotide sequence of the checking primer so as to induce mismatches at this part, due to the presence (or absence) of mutations and polymorphisms to be detected in the present invention.

According to the present invention, extensive amplification is not achieved when a reaction from the end structure of the product, that are produced at early stages of the reaction, is not repeated many times. Thus, even if erroneous synthesis occurs, extensive amplification will not be achieved with mismatches, because the complementary strand synthesis in the amplification is inhibited at some of the stages. As a result, the mismatches effectively suppress the amplification to give a correct result. Namely, the nucleic acid amplification according to the present invention has a nucleotide sequence checking-mechanism with a higher degree of perfection. These features give an advantage over methods, for example, such as PCR, wherein simply sequences between two regions are amplified.

Further, the region X1c, which is characteristic of the primer-used in the present invention, only serves as the origin when a complementary sequence is synthesized, and the complementary sequence anneals to the newly synthesized X1 within the same sequence to proceed the synthesis reaction using the strand itself as the template. Therefore, the primer of the present invention are free from forming loops which is often a serious problem in prior arts even if a so-called primer dimer is generated. Accordingly, non-specific amplification due to a primer dimer does not occur in the present invention, which contributes to the improvement of the reaction specificity.

The two regions, X2c and X1c (or X2 and X1 of the nucleic acid which serves as the target nucleotide sequence), may be linked to each other or may exist separately. The state of the loop portion formed by self-annealing of the product nucleic acid depends on the relative position of the two regions. Further, the two regions preferably are not unnecessarily separated to achieve self-annealing of the product nucleic acid more preferentially than annealing of two molecules. Thus, a preferred length of the spacer nucleotide sequence between the two regions is typically 0 to 500 nucleotides. However, in some cases, regions existing too close to each other may be disadvantageous for forming a desirable loop by self-annealing. More specifically, a structure that enables annealing of a new primer and a smoothly start of complementary strand synthesis reaction which includes a strand displacement is desired for the loop. Thus, more preferably, the primers are designed so that the distance between the region X2c and the region X1c located on the 5'-side of X2c is 0 to 100 nucleotides, further preferably so that it is 10 to 70 nucleotides. The distance values do not contain the lengths of X1c and X2. The nucleotide length of the loop portion further includes the length corresponding to X2.

The regions X2 and X1c constituting the primer used in the present invention are typically arranged continuously without overlapping to each other to the nucleic acid comprising the above specific nucleotide sequence. Alternatively, if X2 and X1c share a common nucleotide sequence, they may be placed so that they partly overlap to each other. X2 should be placed at the 3'-end without exception to function as a primer. On the other hand, X1c is placed at the 5'-end as described below, to provide a function as a primer to the 3'-end of a complementary strand synthesized using X1c as the template. The complementary strand obtained using the primer as the synthesis origin serves as the template of the reverse complementary strand synthesis in the next step, and finally the primer portion is also copied as the template to the complementary strand. The copied 3'-end contains the nucleotide sequence X1, and anneals to X1c located within the same strand to form a loop. Herein, when the primer at the 5'-end of the template is a checking primer, then X1c anneals to the specific region.

The primer used in the present invention is an oligonucleotide that meets two requirements: (1) having the ability to form a complementary base pair, and (2) providing an —OH group at the 3'-end of the base pair that serves as the complementary strand synthesis origin. The backbone of the primer is not restricted to those composed of phosphodiester bonds. For example, the primer may be a phosphothioate, containing S instead of O as the backbone. Further, the nucleotide may be any nucleotide, so long as it forms a complementary base pair. In general, there are five types of naturally occurring nucleotides, namely A, C, T, G, and U; however, analogues such as bromodeoxyuridine, for example, are also included. The oligonucleotide used in the present invention serves not only as the synthesis origin but preferably acts also as the template of complementary strand synthesis.

The primer used in the present invention consists of nucleotides with appropriate length to enable base pairing with the complementary strand by maintaining required specificity under a given condition in various types of nucleic acid synthesis reactions described below. Specifically, the primer comprises 5 to 200 nucleotides, and more preferably 7 to 50 nucleotides. The minimal length of a primer recognized by known polymerases catalyzing sequence-dependent nucleic acid synthesis is around 5 nucleotides. Thus, the length of an annealing portion is preferably longer than 5 nucleotides. In addition, to ensure the nucleotide-sequence specificity, the primer comprises typically 6 nucleotides or more, preferably 7 nucleotides or more. On the other hand, an overlong nucleotide sequence is difficult to chemically synthesize. Thus, the above-mentioned length of primers are exemplified as the preferred range. The exemplified length of primers correspond only to the portion annealing to the complementary strand. As described below, the oligonucleotide of the present invention can independently anneal to at least two regions. Thus, the exemplified length of primers above should be understood as a length corresponding to the length of each region constituting the primer.

Further, the primer used in the present invention can be labeled with known labeling substances. Such labeling substances include ligands with binding capacity, such as digoxin and biotin; enzymes; fluorescent substances and luminescent substances; and radioisotopes. In addition, techniques are known for converting nucleotides in oligonucleotides to fluorescent analogues (WO 95/05391; Proc. Natl. Acad. Sci. USA, 91, 6644–6648, 1994).

Further, the primer used in the present invention can be immobilized on solid phase. Alternatively, an arbitrary portion of the primer may be labeled with a ligand that has binding capacity, such as biotin, and then can be indirectly immobilized via a binding partner, such as immobilized avidin. When an immobilized primer is used as the synthesis origin, the synthesized nucleic acid product is immobilized on a sold phase, and thus can be readily separated. The separated product may be detected by nucleic acid-specific indicators or by further hybridizing a labeled probe. Alternatively, a nucleic acid fragment of interest can be recovered by digesting the nucleic acid with an arbitrary restriction enzyme.

The primer used in the present invention may contain regions additional to the above-mentioned two regions. X2 and X1c are placed at the 3'-end and 5'-end, respectively, and an arbitrary sequence can be placed between the two regions. Such arbitrary sequence includes, for example, a restriction enzyme recognition sequence, a promoter recognized by RNA polymerase, a DNA encoding ribozyme, etc. The single-stranded nucleic acid, synthesis product of the present invention, wherein complementary nucleotide sequences are alternately connected can be digested to two double-stranded nucleic acids with identical length by inserting a restriction enzyme recognition sequence. By inserting a promoter sequence recognized by RNA polymerase, the synthesized product of the present invention can be transcribed into RNA using the product as the template. Furthermore, by additionally arranging a DNA encoding a ribozyme, it is possible to establish a self-cleaving system of the transcripts. All of the additional nucleotide sequences mentioned above function only when the sequences are formed to double stranded nucleic acids. Accordingly, these sequences do not function in the single-stranded nucleic acid of the present invention forming a loop. The additional sequences function for the first time only after the nucleic acid extension proceeds and the sequence anneals to a complementary nucleotide sequence without forming any loop.

The above-mentioned reaction steps (a) to (f) of the present invention will be more specifically described below.

First, complementary strand synthesis using the target nucleotide sequence as the template is performed using the first primer, which primer has the same sequence as that of an arbitrary region in the target nucleotide sequence at the 5'-side. Then, complementary strand synthesis with the second primer is conducted using the elongation product as the template. The region where the annealing of the primer occurs is put to a state ready for base pairing to enable complementary strand synthesis with the second primer. Specifically, this can be achieved by a displacement which accompanies the complementary strand synthesis using a third primer, that anneals to a region of the target nucleotide sequence located on the 3'-side of the region where the first primer anneals, as the origin. According to the present invention, the third primer anneals to a region placed to the 3'-side where the first primer anneals, and serves as the origin of complementary strand synthesis which proceeds toward the region to which the first primer anneals. The step is catalyzed by a DNA polymerase catalyzing complementary strand synthesis which includes strand displacement. Moreover, products elongated from the first primer can be converted to single strands by methods such as heat-denaturation.

Then, elongation products of the second primer initiate complementary strand synthesis using the 3'-end thereof as the primer and the products themselves as the template. A nucleotide sequence complementary to the predicted nucleotide sequence in the arbitrary region of the elongation products from the first primer will be added to the 5'-end of the first primer that was used as the template in the complementary strand synthesis using the second primer. Thus, substantially the same nucleotide sequence as that of the above-mentioned arbitrary region will be contained at the 3'-end of the elongation products from the second primer, which is produced using the first primer as the template.

During this step, the 3'-end of the elongation products from the second primer and the region to which the 3'-end anneals should be prepared ready for base pairing. Typically this step is achieved by converting the elongation products to single strands. Specifically, the elongation products are converted to single strands, for example, by a displacement associated to complementary strand synthesis using a fourth primer as the origin, which primer anneals to the 3'-side of the region where the second primer anneals. Herein, a primer for displacement, such as the third primer mentioned above and the fourth primer used in this step, is referred to as outer primer.

The second primer contains on the 5'-end a nucleotide sequence complementary to a predicted nucleotide sequence within a specific region. Namely, the second primer is a checking primer. The complementary nucleotide sequence is introduced by a primer. Therefore, a sequence synthesized using the second primer as the template contains at the 3'-end a nucleotide sequence complementary to its own specific region. Thus, the system stands ready to check the nucleotide sequence in the specific region. Then, the nucleotide sequence is actually "checked" in subsequent reaction step.

The checking reaction for nucleotide sequences proceeds as follows. First, both of the 3'-end of the single-stranded polynucleotide synthesized above and the specific region are prepared ready for base pairing. This step is preferably achieved as follows. Specifically, the 3'-end is displaced via complementary strand synthesis using the loop forming region with a hairpin structure as the origin.

According to a preferred embodiment of the present invention, a nucleotide sequence for loop formation is placed between the complementary nucleotide sequences of the single-stranded polynucleotide. The sequence for loop formation is designated herein as loop forming sequence. The above-mentioned single-stranded polynucleotide substantially consists of complementary nucleotide sequences linked via the loop forming sequence. In general, a nucleotide sequence that does not dissociate to two or more molecules after the dissociation of base pairs is called a single strand, regardless of whether it still contains partial base pairing or not. Complementary nucleotide sequences can form base pairs even if they exist on the same strand. A product with intramolecullar base pairing, which can be obtained by allowing the above-mentioned single-stranded polynucleotide to form base pairs within the same strand, contains a double-stranded region and a loop portion without base pairing.

Namely, the single-stranded polynucleotide can also be defined as a single-stranded nucleic acid which contains complementary nucleotide sequences annealing to each other in the same strand, and whose annealing products contains a loop without base pairing in the bent hinge portion thereof. Nucleotides with complementary nucleotide sequences can be annealed to the loop which is free from base pairing. The loop forming sequence can be an arbitrary nucleotide sequence. The loop forming sequence can form base pairs to initiate complementary strand synthesis for strand displacement, and preferably contains a sequence which can be distinguished from other nucleotide sequences to enable specific annealing. For example, in a preferred embodiment, the loop forming sequence contains a nucleotide sequence complementary to the first primer. FIG. 5 depicts a schematic illustration wherein FA is annealed to the loop forming region.

Complementary strand synthesis by annealing the first primer to the loop forming region displaces the hybridizing portion of the single-stranded polynucleotide to prepare the specific region and the 3'-end of the single-stranded polynucleotide ready for base pairing. The specific region and the 3'-end of the single-stranded polynucleotide anneal together and the 3'-end provides a 3'-OH serving as the origin of complementary strand synthesis. At this stage, the specific region wherein the nucleotide sequence should be checked is annealed to the 3'-end. Thus, when the nucleotide sequence in this region is the same as the predicted nucleotide sequence, complementary strand synthesis proceeds using the 3'-end as the origin. Alternatively, when the sequence is not the predicted nucleotide sequence, the complementary strand synthesis is inhibited.

A most important feature of the present invention is that the nucleotide sequence checking-mechanism functions over and over again in subsequent reactions by utilizing the LAMP method. For example, even if complementary strand synthesis proceeds despite the difference of the nucleotide sequence from the predicted one, the products of complementary strand synthesis reaction using the single-stranded polynucleotide of the present invention as the template contains a strand at the 3'-end which is complementary to the specific region. The structure of the product does not change, even after repeating the complementary strand synthesis several times, due to the fact that the product itself has the predicted nucleotide sequence within a specific region of the 5'-end. On the other hand, the specific region to which the 3'-end anneals is copied using the target nucleotide sequence as the template, and therefore, annealing of the two still contains the mismatches. Thus, inhibition further occurs in subsequent rounds including the second-round of the reaction. The nucleotide sequence checking-mechanism according to the present invention can be mentioned as a mechanism which minimizes the influence of erroneous complementary strand synthesis.

As described above, a complementary strand synthesis reaction with a nucleotide sequence checking-mechanism proceeds, when the synthesis is conducted in the presence of a target nucleotide sequence using a primer having a specific structure and DNA polymerase catalyzing complementary strand synthesis which includes a strand displacement. As a result, continuous generation of the complementary strand synthesis products starts if the nucleotide sequence of the specific region is the predicted nucleotide sequence. On the other hand, when the sequence is not the predicted nucleotide sequence, the complementary strand synthesis is markedly inhibited by the nucleotide sequence checking mechanism of the present invention. Thus, when amplification products are detected after a fixed period of time, it can be concluded that the specific region in the sample has the predicted nucleotide sequence.

A nucleic acid obtained by the complementary strand synthesis of the present invention is a nucleic acid that comprises alternately connected complementary nucleotide sequences on a single strand. According to the present invention, the quantity of the produced nucleic acid is correlated to the presence of the predicted nucleotide sequence in the specific region. Namely, the amount of nucleic acids with such conformation produced where the sequence of the specific region is not the predicted nucleotide sequence is reduced compared to the amount thereof where the sequence is the predicted nucleotide sequence. As used herein, a nucleic acid comprising alternately connected complementary nucleotide sequences as a single strand used as an index refers to nucleic acids comprising two nucleotide sequences complementary to each other alternately connected on a single strand.

The product of complementary strand synthesis can be detected by methods known in the art. For example, the specific amplification products of the present invention can be detected as distinct band(s) by analyzing reaction solutions by gel electrophoresis. The amplification products of the present invention consist of a repeated conformation of a target nucleotide sequence and the complementary strand thereof as a unit. Electrophoresis of the products gives ladder-like bands lined with constant spacing. Alternatively, the process of complementary strand synthesis during the reaction can be also monitored by known methods. For example, the accumulation of complementary strand synthesis products can be monitored as fluorescence intensity changes using a fluorescent dye specific to double-stranded nucleic acids, such as ethidium bromide and SYBR Green. An internal standard as follows can be used: when the signal derived from the internal standard is enhanced or reaches plateau and the signal derived from the sample is not substantially enhanced, it indicates that the specific region in the sample does not have the predicted nucleotide sequence.

According to the detection method of the present invention, the amount of products synthesized by complementary strand synthesis can be compared with that of the internal standard. For example, a nucleic acid, which is derived from the same nucleic acid sample but contains neither mutations nor polymorphic changes, can be used as the internal standard. To analyze genomic nucleotide sequences, a genomic nucleotide sequence of which the existence of neither mutations nor polymorphisms are known are used as the internal standard. Alternatively, when the detection method of the present invention is conducted using mRNA as the template, for example, a gene, which is expressed in a wide variety of cells at nearly the same level, can be used as the internal standard. Using the nucleotide sequence of any of these internal standards as the target nucleotide sequence, the reaction of complementary strand synthesis is carried out under the same condition as in the present invention. The amount of the products is compared as a control with that from a nucleotide sequence which is the subject of the mutation detection. When the detected amount of the product is comparable to that of the internal standard, the nucleotide sequence of the specific region is confirmed to have the predicted nucleotide sequence. Conversely, when the nucleotide sequence of the specific region is not the predicted one, the amount of the products of the complementary strand synthesis is smaller than that of the internal standard.

Further, when unexpectedly no product of complementary strand synthesis for the internal standard can be detected or when the amount of the detected product is smaller than expected, trouble in the reaction itself is suspected. In most cases, the reaction of an internal standard is conducted in the same reaction solution as the primers to be tested. However, the internal standard can be assayed separately in the present invention, so long as the reaction is carried out using the same sample under an identical condition. For example, even when the standard and the sample nucleic acid is assayed using an identical sample in a first reaction system and second reaction system, respectively, the standard is called internal standard.

According to the present invention, the number of complementary nucleotide sequences in the synthesized nucleic acid is at least a single pair when the specific region contains the predicted nucleotide sequence. According to a preferred embodiment of the present invention, the number is sometimes integral multiples. In such cases, there is theoretically no upper limit on the number of pairs of complementary nucleotide sequences in the above-mentioned nucleic acid of the present invention. When the nucleic acid synthesized as the product of the present invention consist of multiple pairs of complementary nucleotide sequences, the nucleic acid consists of a repetition of identical nucleotide sequence. Needless to say, the reaction products may include those pre-maturely terminated without reaching the 5-end during the reaction of complementary strand synthesis along the template.

The nucleic acid comprising complementary nucleotide sequences alternately connected as a single strand, which is synthesized according to the present invention, does not always have to have the same structure as that of natural nucleic acids. A nucleic acid derivative is known to be synthesized by the use of nucleotide derivatives as a substrate in nucleic acid synthesis with DNA polymerase. Such nucleotide derivatives include nucleotides labeled with radioisotope and nucleotide derivatives labeled with a ligand with binding capacity, such as biotin and digoxin. Labeling of nucleic acid derivatives as the products can be achieved using such nucleotide derivatives. Alternatively, the product can be obtained as a fluorescent nucleic acid derivative using a fluorescent nucleotide as a substrate. Further, the product may be DNA or RNA. Whether DNA or RNA is produced depends on the combination of primer structure, type of polymerization substrate, and type of polymerization reagent used in the nucleic acid polymerization.

The nucleic acids used in the present invention may be DNA, RNA, or chimeric molecules thereof. The nucleic acids may be natural nucleic acids, as well as artificially synthesized nucleic acids. Further, nucleotide derivatives having partially or completely artificial structure are also included in the nucleic acids of the present invention, so long as it can form base pairs or function as a template in complementary strand synthesis. There is no limitation on the number of nucleotides in the nucleic acid of the present invention. The term nucleic acid is equivalent to the term polynucleotide. On the other hand, the term oligonucleotide herein especially refers to polynucleotides with smaller number of nucleotides among polynucleotides. Typically, the term oligonucleotide refers to polynucleotides containing 2 to 100 nucleotide residues, more typically about 2 to 50 nucleotide residues, but is not limited thereto.

The detection method of the present invention can be used for all types of nucleic acids. Specifically, for example, such nucleic acids include genomic DNAs of prokaryotic and eukaryotic cells; viral genome DNA and RNA; genomes of intracellular parasites, such as *Mycoplasma* and *Rickettsia*; cDNAs converted from mRNAs derived from these species; libraries constructed from these gene sources; clones isolated from the libraries; and so on. When the gene tested for mutations and polymorphic changes is RNA, it can be converted to cDNA using a DNA polymerase with reverse transcriptase activity. The nucleic acid used as a sample of the present invention is generally contained in a biological sample. Such biological samples include tissues of animals and plants, cells of microorganisms, cells, cultures, excrements, and extracts thereof. According to the present invention, nucleic acids contained in these biological samples derived from organisms, and those originating from infectious parasites, microorganisms, and viruses living in the organisms as hosts can be used as the subject of detection. The nucleic acid of the present invention can be also derived from the nucleic acids in the above-mentioned biological samples. For example, cDNA synthesized from mRNA and nucleic acid amplified from a nucleic acid derived from a biological sample can be used as a sample in the detection method of the present invention. These genes can be used as samples in the detection method of the present invention, after denaturation to single strands, or kept double-stranded as follows.

A nucleic acid containing the target nucleotide sequence of the present invention can be used as the sample, in the form of a double strand, when it is incubated under a condition suitable for primer annealing and for complementary strand synthesis using the primer as the origin. In general, the step of conversion to single strands by denaturation is required to analyze a nucleic acid sample by hybridization to a probe or primer. However, the present inventors have discovered that the step of conversion to complete single strands can be omitted during complementary strand synthesis from a primer under conditions wherein double-stranded nucleic acids are destabilized (Japanese Patent Application No. 2000-111939 filed Apr. 7, 2000).

Specifically, efficient complementary strand synthesis is difficult under a condition wherein double-stranded nucleic acids are destabilized alone, but by combining the synthesis with nucleic acid amplification reaction which originally proceeds under an isothermal condition, amplification with a similar efficiency as that achieved using single-stranded nucleic acid templates is enabled. The nucleic acid amplification method applicable to the present invention proceeds isothermally when the used template nucleic acids are single-stranded. The method is based on the principle of reaction cycling of complementary strand synthesis under an isothermal condition consisting of the steps of self-annealing and subsequent complementary strand synthesis, and the renewed primer annealing to the loop and the subsequent complementary strand synthesis using DNA polymerase catalyzing complementary strand synthesis which comprises strand displacement. Thus, according to the present invention, a double-stranded nucleic acid can be used as the target nucleotide sequence.

Methods for detecting mutations and polymorphisms using a double-stranded nucleic acid directly as a template according to the present invention are described herein. The following description explains the process of complementary strand synthesis initiated when the nucleotide sequence of the specific region is the predicted nucleotide sequence. When the nucleotide sequence in the specific region differs from the predicted nucleotide sequence, a step inhibiting the reaction of complementary strand synthesis that proceeds using the strand itself as the template after the 3'-end of the strand itself anneals to the specific region, is incorporated into some types of reactions of complementary strand synthesis described below.

The double-stranded nucleic acid of the present invention includes, for example, cDNA and genome DNA. In addition, various vectors in which these DNAs have been inserted can be also used as the double-stranded nucleic acid of the present invention. The double-stranded nucleic acid of the present invention may be purified or crude nucleic acids. Moreover, the method of the present invention are also applicable to nucleic acid in cells (in situ). In-situ genomic analysis can be achieved using the double-stranded nucleic acid in cells as the template.

When a cDNA is used as the template in the present invention, the step of cDNA synthesis and the method of nucleic acid synthesis according to the present invention can be carried out under the same conditions. When first strand synthesis of cDNA is carried out using RNA as the template, a double-stranded nucleic acid of DNA-RNA hybrid is formed. The method for synthesizing nucleic acids can be conducted-using the double-stranded nucleic acid as the template of the present invention. When the DNA polymerase used in the method for synthesizing the nucleic acid of the present invention has a reverse transcriptase activity, the nucleic acid synthesis can be achieved using a single enzyme under the same condition. For example, Bca DNA polymerase is a DNA polymerase having strand-replacing activity as well as reverse transcriptase activity. As a matter of course, the method for synthesizing nucleic acids according to the present invention can be also used after the formation of complete double-stranded cDNA by the second strand synthesis.

A polymerase catalyzing complementary strand synthesis which comprises strand displacement is used to detect mutations and polymorphisms according to the present invention. The same type of polymerases as those used for SDA and such can be used as the DNA polymerase of the present invention. A specific polymerase which synthesizes complementary strands by replacing the double-stranded region at the 5'-side of the template, if any double stranded region exists on the template, during complementary strand synthesis using a primer complementary to a region at the 3'-side of a certain nucleotide sequence as the synthesis origin is known in the art. The 5'-side of the template represents a region located at the 3'-side of the primer. Thus, the 5'-side of the template is the direction to which the reaction of complementary strand synthesis proceeds. According to the present invention, substrates required for complementary strand synthesis are further added.

An arbitrary primer is mixed with the double-stranded nucleic acid in the present invention, and the mixture is incubated under a condition ensuring the complementary strand synthesis using the primer as the origin. The arbitrary primer of the present invention is used to allow the region to which FA will anneal to become ready for base pairing. Thus, the arbitrary primer is required to have the ability to anneal to the complementary strand of the nucleotide strand, to which FA anneals, of the template double-stranded nucleic acid. Further, the strand extension in the complementary strand synthesis using the arbitrary primer of the present invention as the replication origin should proceed toward the region to which FA anneals. In other words, the primer can anneal to an arbitrary portion of the region, which region serves as the template in a complementary strand synthesis using FA as the origin. The arbitrary primer can be selected from arbitrary regions so long the presence of buffer giving a pH suitable for the enzyme reaction, salts required for primer annealing and maintaining the catalytic activity of the enzyme, preservatives for the enzyme, and in addition if needed, a melting temperature (Tm) regulator, and such. The buffer with a buffering action in a range from the neutral to weak alkaline pH, such as Tris-HCl, is used in the present invention. The pH is adjusted depending on the type of DNA polymerase used. Examples of salts to be added to maintain the enzyme activity and to modify the melting temperature (Tm) of nucleic acid include KCl, NaCl, $(NH_4)_2SO_4$, etc. The enzyme preservatives include bovine serum albumin and sugars.

Further, typical melting temperature (Tm) regulators include betaine, proline, dimethylsulfoxide (hereinafter abbreviated as DMSO), and formamide. When a melting temperature (Tm) regulator is used, annealing of the above-mentioned oligonucleotide can be regulated within a limited temperature range. Moreover, betaine (N,N,N-trimethylglycine) and tetraalkylammonium salts effectively contribute to the improvement of the efficiency of strand displacement due to its isostabilizing action. The addition of betaine at a concentration of about 0.2 to 3.0 M, preferably about 0.5 to 1.5 M to the reaction solution is expected to enhance the amplification of nucleic acids of the present invention. Since these melting temperature regulators decrease the melting temperature, a condition giving desired stringency and reactivity is empirically chosen by considering reaction conditions, such as salt concentration and reaction temperature.

Suitable temperature conditions for enzyme reactions can be readily chosen by utilizing a Tm regulator. Tm alters depending on the relation of the primer and target nucleotide sequence. Thus, it is preferable to adjust the amount of a Tm regulator so that the conditions that maintain the enzyme activity are consistent with the incubation conditions that meet the criterion of the present invention. Based on the disclosure of the present invention, those skilled in the art can readily as it meets the criterion. For example, an outer primer (described hereinafter), which anneals on the 3'-side of RA or the region where RA anneals within the template, can be also used as the arbitrary primer. The use of the outer primer is one of the preferred embodiments of the present invention, due to the reduced number of necessary reaction components.

Base pairing with FA can be ensured by displacing one of the two strands of the double-stranded nucleic acid in complementary strand synthesis using the arbitrary primer as the origin. By choosing such a condition, the method of the present invention can be conducted without changing temperature even when a double-stranded nucleic acid is used as the sample. A condition which ensures the annealing of the arbitrary primer and double-stranded nucleic acid, and complementary strand synthesis using this primer as the origin, is practically a condition where the following multiple steps can be achieved without changing the reaction condition:

i) annealing of the primer to a double-stranded nucleic acid template; and ii) proceeding with complementary strand synthesis using the annealing primer as the replication origin.

In general, it was believed that a primer could anneal to a nucleic acid strand only if the region to which the primer anneals is single-stranded. Thus, when a double-stranded nucleic acid is used as a template, the nucleic acid has previously been subjected to a step to convert the nucleic acid to single strands by denaturation prior to the primer annealing. However, the primer annealing can be achieved by incubating the template with the primer under a condition where the double strand is destabilized by a certain means without completely converting the double stand to single strands. A condition under which the double stranded nucleic acid is heated up to nearly the melting temperature (hereinafter abbreviated as Tm) can be exemplified as such double strand destabilizing condition. Alternatively, the addition of a Tm regulator is also effective.

The reaction comprising a series of steps is carried out in choose proper amounts of a Tm regulator to be added, depending on the primer nucleotide sequence. For example, Tm can be determined based on the length of annealing nucleotide sequence and the GC content, salt concentration, and concentration of the Tm regulator.

Annealing of a primer to a double-stranded nucleic acid under such conditions is presumed to be unstable. However, the complementary strand synthesis proceeds using the unstably annealed primer as the replication origin when the DNAs are incubated with a DNA polymerase catalyzing the complementary strand synthesis which includes strand displacement. Once a complementary strand is synthesized, primer annealing becomes more stable over time. The DNA polymerases listed below catalyze the complementary strand synthesis under conditions ensuring the primer to anneal to the double-stranded nucleic acid.

A DNA polymerase catalyzing complementary strand synthesis which includes strand displacement plays a central role in the method for detecting mutations and polymorphisms of the present invention. Such DNA polymerases include those listed below. In addition, various mutants of these enzymes can be used in the present invention, so long as they have the activity of sequence-dependent complementary strand synthesis and the strand replacing activity. Such mutants include truncated enzymes having only the structures with the catalytic activity or mutant enzymes whose catalytic activity, stability, or thermal stability has been modified by amino acid mutations, and such.

Bst DNA polymerase

Bca(exo-) DNA polymerase

Klenow fragment of DNA polymerase I

Vent DNA polymerase

Vent(Exo-) DNA polymerase (exonuclease activity-free Vent DNA polymerase)

DeepVent DNA polymerase

DeepVent(Exo-) DNA polymerase (exonuclease activity-free DeepVent DNA polymerase)

Φ29 phage DNA polymerase

MS-2 phage DNA polymerase

Z-Taq DNA polymerase (Takara Shuzo)

KOD DNA polymerase (TOYOBO)

Among these enzymes, Bst DNA polymerase and Bca (exo-) DNA polymerase are particularly preferred, because they are enzymes with thermal stability to a degree and high catalytic activity. According to the present invention, the annealing of a primer to a double-stranded nucleic acid and complementary strand synthesis are conducted under the same condition. Since such reaction often requires some heating, the use of thermostable enzymes is preferred. The reaction can be achieved under a wide variety of conditions by thermostable enzymes.

For example, Vent(Exo-) DNA polymerase is a highly thermostable enzyme that has strand replacing activity. It has been reported that the addition of a single strand-binding protein accelerates the reaction of complementary strand synthesis by DNA polymerase which comprises strand displacement (Paul M. Lizardi et al., Nature Genetics 19, 225–232, July, 1998). By applying the method to the present invention, acceleration of complementary strand synthesis is expected by the addition of single strand-binding protein. When Vent(Exo-) DNA polymerase is used, T4 gene 32 is effective as the single strand-binding protein.

A phenomenon where the complementary strand synthesis is not terminated even when the reaction reaches the 5'-end of the template and an extra nucleotide is added to the synthesized strand is known in the art due to the use of a DNA polymerase lacking 3'–5' exonuclease activity. Such a phenomenon is not preferable in the present invention, because the next complementary strand synthesis initiates from the synthesized 3'-end complementary strand sequence. However, the nucleotide added to the 3'-end by the DNA polymerase is nucleotide "A" with high probability. Thus, a sequence for complementary strand synthesis should be selected so as to initiate synthesis from the 3'-end from A to avoid problems by the erroneous addition of a single-dATP nucleotide. Alternatively, even when the 3'-end protrudes during complementary strand synthesis, it can be digested to a blunt end by a 3'→5' exonuclease activity. For example, the natural Vent DNA polymerase, which has such activity, can be used in combination with Vent(Exo-) DNA polymerase to overcome the problem.

Unlike the DNA polymerases described above, DNA polymerases, such as Taq polymerase PCR which are routinely used in PCR and such, exhibit substantially no activity of strand displacement under typical conditions. However, such DNA polymerases can be also used for the present invention, when they are used under conditions ensuring strand displacement.

According to the present invention, a loop primer can be used to improve the amplification efficiency in the LAMP method. The loop primer is a primer providing an origin for complementary strand synthesis between a region derived from FA in the elongation products of the above-mentioned FA and the arbitrary region corresponding to FA (namely, the region comprising the nucleotide sequence complementary to the 5'-end of FA). Likewise for RA, it is possible to use a loop primer providing an origin for complementary strand synthesis between a region derived from RA in the elongation products of the above-mentioned RA and the arbitrary region corresponding to RA (namely, the region comprising the nucleotide sequence complementary to the 5'-end of RA). Herein, for convenience sake, the loop primer corresponding to FA is referred to as loop primer F; the loop primer corresponding to RA is referred to as loop primer R. The loop primer was designed based on the fact that the products by the LAMP method often include loops to which neither RA nor FA can anneal. The present inventors filed a patent application on the LAMP method using a loop primer (filed Sep. 19, 2000; Japanese Patent Application No. 2000-283862). The reaction efficiency is markedly improved by the combined use of a loop primer with the LAMP method. In cases of using a loop primer, the reaction is initiated after adding a loop primer F and/or loop primer R together with RA, FA, and if required, the outer primer. The effect by a loop primer may be expected even by the addition of the loop primer alone after the reaction proceeds, however, it is more rational to add them prior to starting the reaction to improve the reaction efficiency.

According to the present invention, a kit can be provided as a set of pre-combined components of the above-mentioned reaction of the present invention. More specifically, the present invention relates to a kit for detecting mutations and/or polymorphisms, which comprises a primer set consisting of two inner primers, DNA polymerase catalyzing complementary strand synthesis which includes strand displacement, and nucleotide substrates, in which at least either of the inner primers of the above-mentioned primer set is a checking primer. An outer primer corresponding to the above-mentioned inner primer and another primer set for the internal standard can be incorporated in the kit of the present invention. Further, the kit may also contain loop primers to improve the reaction efficiency. Furthermore, standard samples as positive or negative controls, direction for instruction, and such, may be attached to the kit. Moreover, the kit may contain an indicator component for detecting amplification products. Such indicators include, for example, fluorescent dyes such as EtBr; probes generating signals when recognizing the nucleotide sequence of amplification products; and so on.

Furthermore, a genotyping kit for determining heterozygte/homozygote can be provided by the combined use of two primer sets for wild type and mutant type as the above-mentioned inner primer sets. When different types of mutations are tested with the genotyping kit, homozygote and heterozygote can be discriminated for all mutations by genotyping using multiple primer sets corresponding to the number of mutation types. Determining homozygote and heterozygote is important in pedigree analysis and genotype-based phenotype prediction.

The basic principle of the amplification reaction for double-stranded nucleic acids by the combined use of the above-mentioned inner primers, RA and FA, and DNA polymerase having strand-replacing activity is described below referring to FIGS. 1 to 4. According to the example, the amplification primer set consists of the inner primers, RA and FA, and further, RA serves as an arbitrary primer allowing a region of the double-stranded target nucleotide sequence, to which FA anneals, to make ready for base pairing. An amplification reaction as described below proceeds in the present invention, when the specific region, namely R1, comprises the predicted nucleotide sequence. On the other hand, if the specific region does not have the predicated nucleotide sequence, the reaction of complementary strand synthesis is inhibited every time when the 3'-end R1c anneals to R1, and thus theoretically, the amplification reaction does not proceed. Alternatively, even when complementary strand synthesis erroneously proceeds using R1c as the origin with a certain probability, the ultimate influence is assumed to be negligible because the amount of the products is very small.

The above-mentioned arbitrary primer (RA in FIG. 1-(1)) first anneals to X2c (corresponding to R2c) on the template double-stranded nucleic acid to serve as the origin of complementary strand synthesis. Under such condition, the double-stranded nucleic acid is unstable and the primer directly serves as the origin of complementary strand synthesis on the double-stranded nucleic acid. In FIG. 1-(2), the complementary strand synthesized using RA as the origin displaces one of the strands of the template double-stranded nucleic acid, and F2c, which is the region annealing with inner primer FA, becomes ready for base pairing (FIG. 1-(2)).

A complementary strand synthesis is conducted by annealing FA to the region F2c which is ready for base pairing. Herein, an outer primer F3, which initiates complementary strand synthesis from the 3'-side of FA, also anneals to the region (FIG. 2-(4)). The outer primer are designed so as to initiate the complementary strand synthesis on the 3'-side of each inner primer, and is used at a lower concentration than those of the inner primers. Thus, the outer primer initiates with high expectance a complementary strand synthesis with a lower probability as compared with the inner primers.

The stringency of the checking mechanism in the mutation detection method of the present invention using a loop primer in combination with inner primers, RA and FA, chiefly depends on Tm of F1/F1c. A stringent nucleotide sequence-checking mechanism can be achieved by minimizing Tm of F1/F1c within an allowable range. However, in cases where the Tm of F1/F1c is lower than the acceptable limit, efficient amplification cannot be expected even when the nucleotide sequence in the specific region is the predicted nucleotide sequence. For example, in the Example described below, efficient synthesis occurs at a reaction temperature of 60° C. when the Tm of F1/F1c is 45° C. Generally, hybridization of different polynucleotide molecules cannot be expected when the reaction temperature is 15° C. higher than Tm. In other words, efficient complementary strand synthesis is not expectable in such cases. However, since annealing of F1/F1c occurs on a single molecule in the present invention, the checking of nucleotide sequences can be achieved with enough stringency without sacrificing reaction efficiency even when the Tm is a little lower than the reaction temperature. Thus, a condition where the Tm of F1/F1c is designated so that different types of polynucleotides are incapable of hybridizing to each other but where the intramolecular hybridization is possible is advantageous for the present invention. For example, the Tm values of the respective primers used in Example 5 described hereinafter are as follows:

Outer primer F3 (R3): 60° C.
Loop primer FL: 56° C.
Loop primer RL: 58° C.
F2 on the 3'-side of the inner primer FA (or R2 on the 3'-side of RA): 55° C.
F1c on the 5'-side of the inner primer FA (or R1c on the 5'-side of RA): 45° C.

Overall reaction efficiency increases when the loop primer is used in combination according to the present invention. Therefore, extensive amplification in a short period is expected even with the Tm of F1c (R1c) is set lower. Thus, the lengths of the primers can be shortened according to the present invention.

As a result of complementary strand synthesis using the outer primer F3 as the origin, the elongation product synthesized using the inner primer FA as the origin is displaced and released as a single strand (FIG. 2-(5)). Using this single strand as the template, RA and the outer primer R3 corresponding to RA anneal to each other and initiates complementary strand synthesis (FIG. 3-(6)). As a result, the elongation products from RA have a structure with which the 3'-end F1 can intramolecullarly anneal with itself (FIG. 3-(8)).

In FIG. 3-(6), the 5'-end of the strand is annealed intramolecullarly to itself. However, the amplification reaction cannot be initiated with this structure, since the 5'-end does not serve as the origin of complementary strand synthesis. The amplification reaction is initiated only when a complementary strand to the strand shown in FIG. 3-(6) is synthesized, and thereafter a structure which anneals to itself at the 3'-end thereof is provided (FIG. 3-(8)). These reaction steps may be referred to as just preliminary steps for the amplification reaction of the present invention.

Nucleic acid amplification and checking mechanism of the nucleotide sequence at specific region R1c according to the present invention are specifically described below, with reference to the schematic illustration depicted in the Figures. The self-annealed 3'-end F1 (FIG. 3-(8)) serves as the origin of complementary strand synthesis. Annealing to the 3'-end occurs between F1 and F1c, and thus, there is the possibility that the annealing competes with FA that also contains F1c. However, in actual, the complementary nucleotide sequences F1/F1c which exist in a neighboring region on an identical strand preferentially anneal to each other. Thus, the reaction of complementary strand synthesis using its own strand as the template is preferentially initiated. The nucleic acid in which the target nucleotide sequence has been alternately connected on a single strand is synthesized through this reaction. Further, F2c, to which the inner primer FA can anneal, is present in a loop forming region that is formed by the self-annealing of the 3'-end F1. After FA anneals to this portion, complementary strand synthesis is initiated (FIG. 3-(8)). The positional relation of the loop portion annealing to the inner primer FA is depicted in FIG. 5. Complementary strand synthesis from FA annealing to the loop displaces the products of complementary strand synthesis initiated from the 3'-end using itself as the template, and again the 3'-end R1 is allowed to become ready for self-annealing (FIG. 4-(9)). The subsequent reaction comprises the alternate steps of complementary strand synthesis using the 3'-end of itself as the origin and its own strand as the template, and complementary strand synthesis using the loop portion as the origin and the inner primer RA as the origin. As described above, the nucleic acid amplification reaction comprises the alternate steps of repeated 3'-end extension using its own strand as the template and newly initiated extension from the primer annealing to the loop portion.

On the other hand, regarding the nucleic acid strand synthesized complementary to the single-stranded nucleic acid, that is extended using its own strand as the template, using the oligonucleotide annealing to the loop portion thereof as the origin, synthesis of a nucleic acid having a complementary nucleotide sequence alternately connected on a single strand also proceeds on the synthesized nucleic acid strand. Specifically, the complementary strand synthesis from the loop portion is completed, for example, when it reaches R1 as depicted in FIG. 4-(9). Then, another complementary strand synthesis is newly initiated using the 3'-end displaced by the nucleic acid synthesis as the origin (FIG. 4-(9)). Eventually, the reaction reaches the loop portion that has been the origin of synthesis in the previous steps to initiate the displacement again. Thus, the nucleic acid that initiated the synthesis from the loop portion is also displaced, and as a result the 3'-end R1 annealing on the strand itself is produced (FIG. 4-(11)). This 3'-end R1 initiates complementary strand synthesis after annealing to R1c present on the same strand. When F in this reaction is considered as R and R as F, the reaction is the same as that depicted in FIG. 3-(8). Thus, the structure depicted in FIG. 4-(11) serves as a new nucleic acid that continues the self-extension and another nucleic acid synthesis.

As described above, according to the method of the present invention, the reaction that continuously provides nucleic acids that initiate another extension proceeds together with the elongation of a nucleic acid. As the strand is further extended, multiple loop-forming sequences are generated not only at the strand end but also within the same strand. When these loop-forming sequences become ready for base pairing through the synthesis reaction which comprises strand displacement, the inner primers anneal to the loop-forming sequences and serves as synthesis origins for producing new nucleic acids. More efficient amplification is achieved by combining synthesis initiated from internal regions of the strand to the strand synthesis from the strand end.

Further, the check frequency by the checking mechanism may be increased by adopting a checking primer as not only RA but also as FA in the present invention. Alternatively, even when the nucleotide sequence in the specific region is checked with only the 3'-end produced using RA as the template, the reaction of complementary strand synthesis proceeds through the checking of the nucleotide sequence of the specific region. As a result, the amount of products generated in the complementary strand synthesis where the specific region has not the predicted nucleotide sequence is greatly reduced as compared to that where the specific region has the predicted nucleotide sequence. Thus, the present invention provides a method for detecting mutations and/or polymorphisms, which is excellent in S/N ratio based on the principle.

As described above, strand extension accompanying synthesis of new nucleic acids can be achieved by the use of primers having specific structures. Further, according to the present invention, the newly generated nucleic acids themselves extend, and results in a new generation of other nucleic acids. Theoretically, this series of reaction continues endlessly, and thus can achieve extremely efficient nucleic acid amplification. In addition, the method of the present invention can be conducted under an isothermal reaction condition.

In cases where RA and FA are used as the inner primers in the present invention, an important feature is that the series of reaction steps proceed only when the position of the multiple regions to each other is constantly maintained. Further, in embodiments where the outer primer is used in combination, at least six regions are involved in the reaction. Due to this feature, non-specific synthesis accompanying non-specific complementary strand synthesis can be effectively prevented. Specifically, this feature contributes to the reduction in the probability that the product will serve as a starting material in a subsequent step of amplification even when some non-specific reaction occurs.

Furthermore, the fact that process of the reaction is controlled by a plurality of different regions provides one with the flexibly to construct a detection system that ensures precise discrimination of similar nucleotide sequences. It is an important task to detect SNPs between similar nucleotide sequences of genes, such as human CYP2C19. However, it has been difficult to detect minor mutations in similar nucleotide sequences by a single-round of amplification reaction according to conventional gene amplification techniques, such as PCR, and other known signal amplification techniques, such as the Invader method. According to the present invention, the primers can be designed so as to ensure extensive amplification when multiple regions contain the predicted nucleotide sequences and maintain specific positional relationship.

Thus, the present invention is useful for detecting minor differences in nucleotide sequences between multiple genes containing similar nucleotide sequences, for example, in typing of HLA and platelet alloantigen, or pathogenic microorganisms. Most part of such genes determining the phenotype is common among the genes, and the typing is carried out based on mutation patterns in some regions. The method of the present invention, wherein a certain amount of amplification products can be only generated when the nucleotide sequences in multiple regions are identical to predicted ones, is suitably used in such analyses.

Further, based on the present invention, heterozygote and homozygote can be clearly discriminated by analyzing genomic DNA of a same sample by a primer, which primer ensures amplification of a nucleotide sequence when the specific region is identical to that of the wild-type, in combination with another primer, that ensures amplification of a sequence which is identical to that of the mutant. Specifically, a sample is a homozygote of either of the wild type or the mutant when the sample is amplified by only either of the primers. On the other hand, a sample is a heterozygote consisting of the mutant and wild-type sequences when amplification by both of the primers is achieved.

Furthermore, the present invention is also useful as a technique for analyzing genes involved in drug metabolism, which may contribute to tailor-made medicine. The genes involved in drug metabolism are important in determining drug-sensitivity of an individual. The differences of the activity of drugs on individuals have been predicted to result from minor differences in the nucleotide sequence of the gene which encodes enzymes involved in the metabolism of the drug. Standard human genes are being revealed by the Human Genome Project. One of the practical applications of the result of the Project is analysis of genes involved in drug metabolism which has become of major interest. Thus, the present invention provides a technique that is highly useful in the post genome age.

All publications describing prior arts cited herein are incorporated by reference.

BRIEF DESCRIPTION OF THE DRAWINGS

FIG. 6 depicts the nucleotide sequences of genes belonging to the human CYP2C19 family, which sequences are similar to one another.

BEST MODE FOR CARRYING OUT THE INVENTION

The present invention is illustrated in detail below with reference to Examples.

Example 1

Detection of Mutations in the Human CYP2C19 Gene (1)

Figure 1:
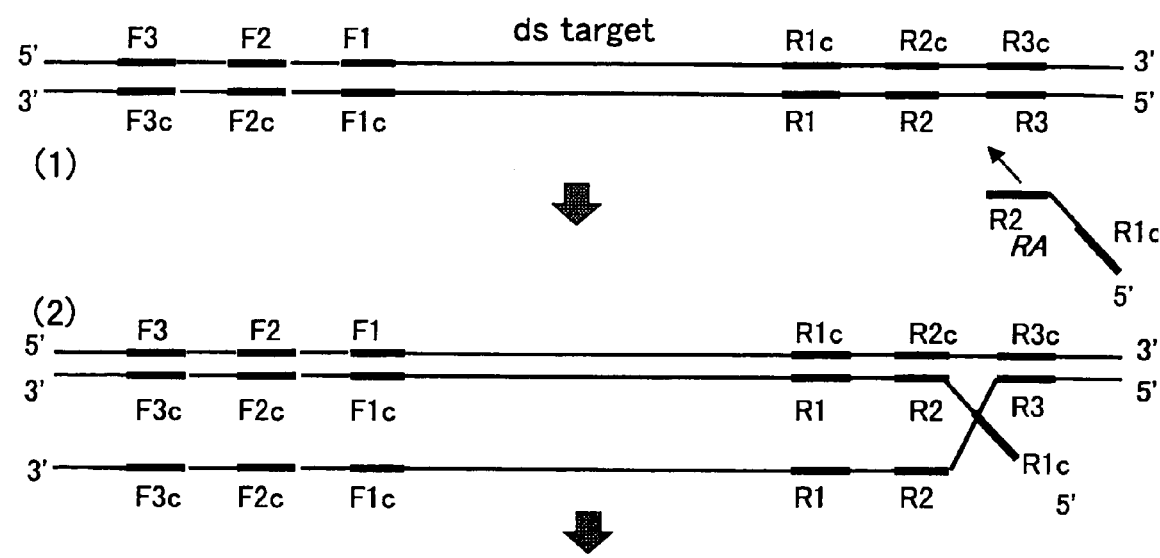
FIG. 1 depicts a schematic illustration demonstrating a part, (1) to (2), of the reaction principle of a preferred embodiment according to the present invention.
Figure 2:
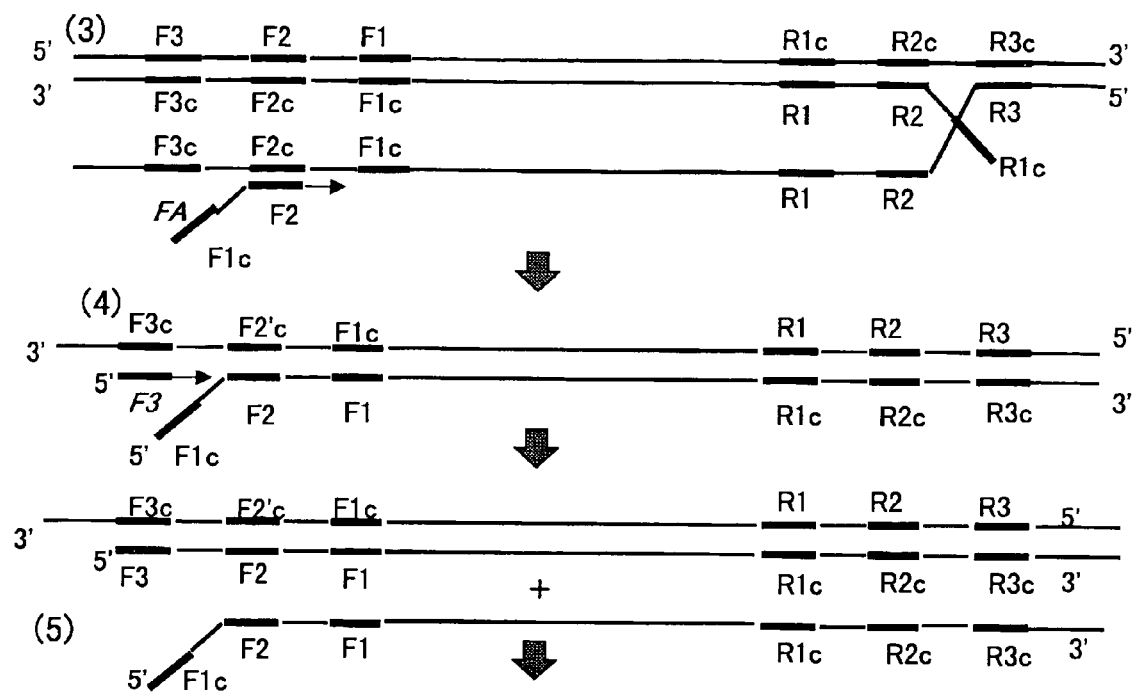
FIG. 2 depicts a schematic illustration demonstrating a part, (3) to (5), of the reaction principle of a preferred embodiment according to the present invention.
Figure 3:
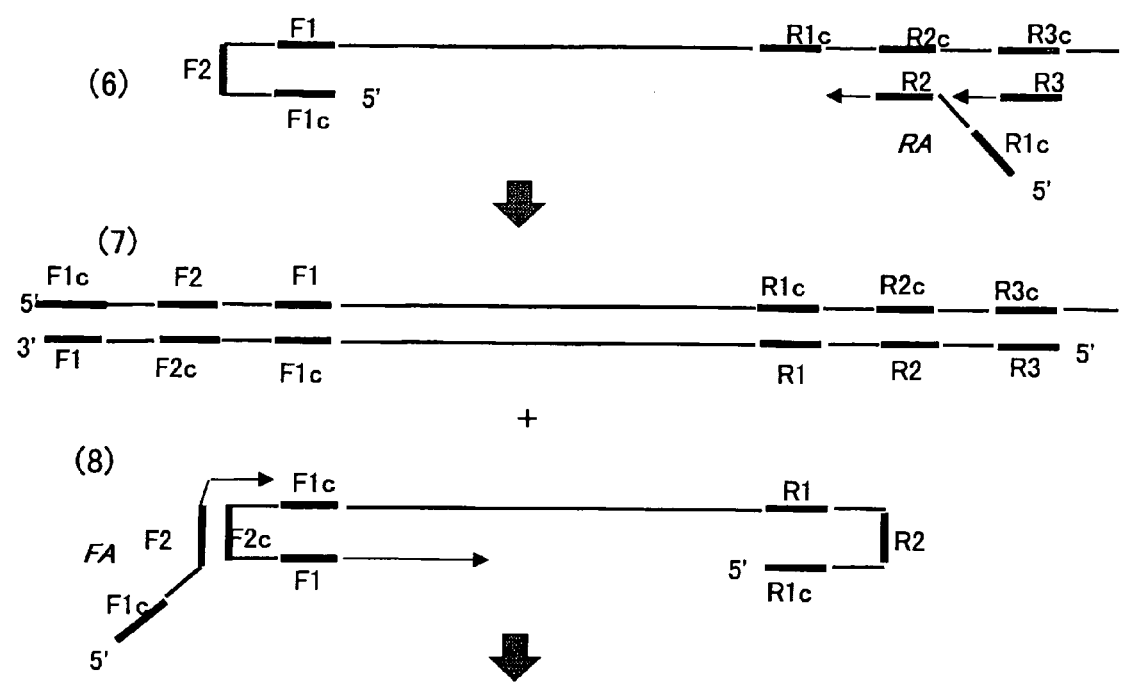
FIG. 3 depicts a schematic illustration demonstrating a part, (6) to (8), of the reaction principle of a preferred embodiment according to the present invention.
Figure 4:
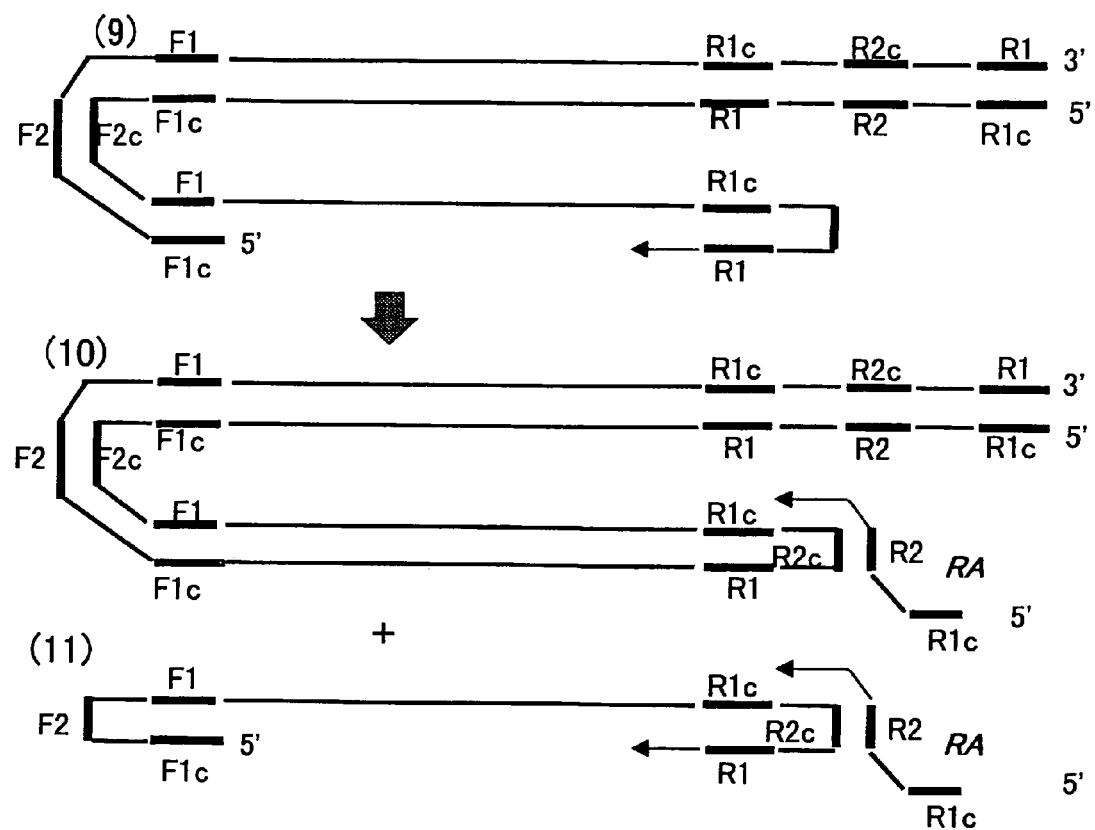
FIG. 4 depicts a schematic illustration demonstrating a part, (9) to (11), of the reaction principle of a preferred embodiment according to the present invention.
Figure 5:
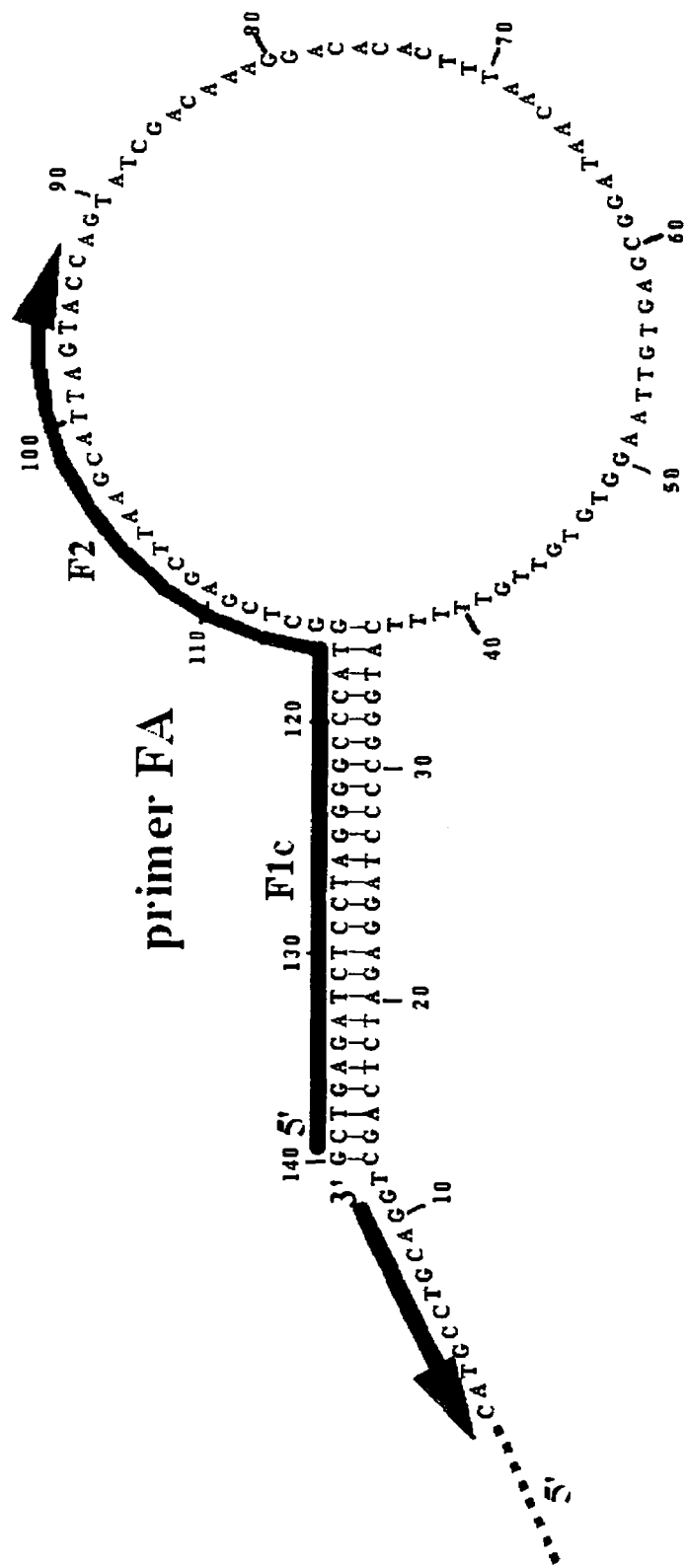
FIG. 5 depicts a schematic illustration of the loop structure formed in the single-stranded nucleic acid of the present invention.
Figure 7:
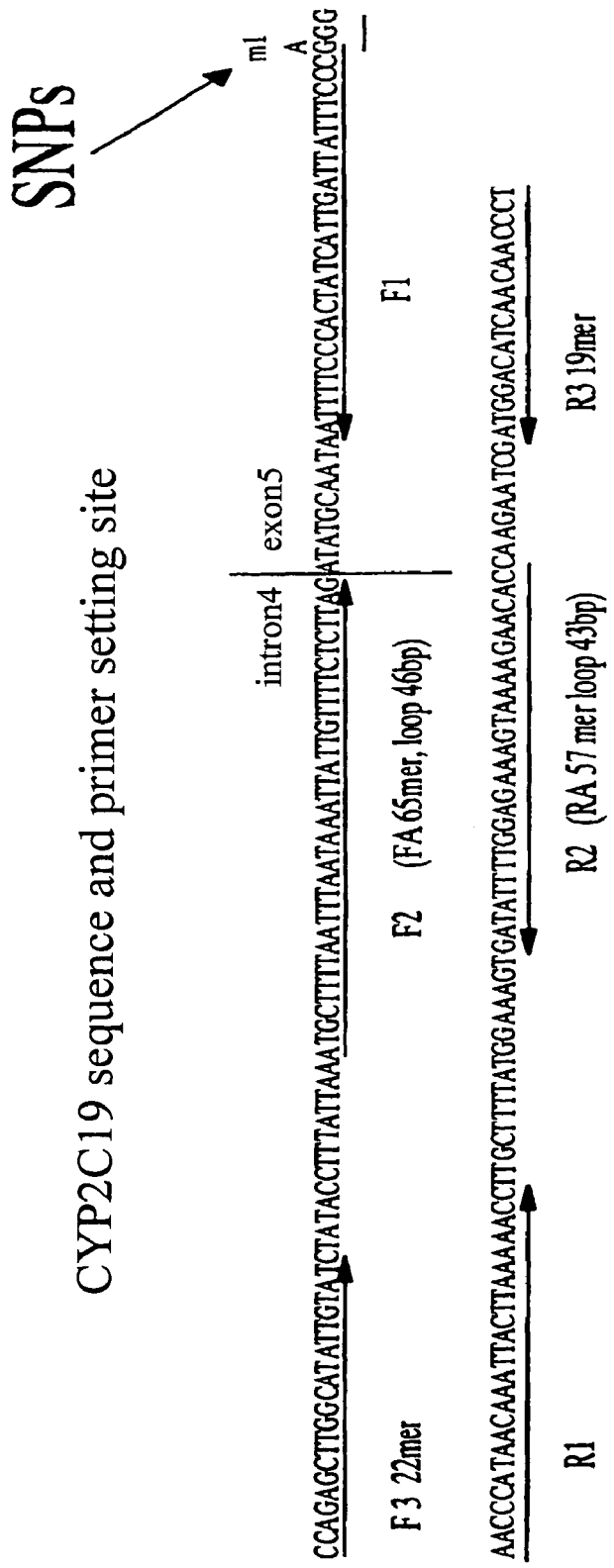
FIG. 7 depicts a schematic illustration demonstrating the target nucleotide sequence, that was used in the detection of SNPs in the Example, and positional relation of primers to the target nucleotide sequence.

The human CYP2C19 gene was amplified by PCR and was digested with restriction enzyme SmaI, which recognizes the site of SNPs, for typing the gene as wild type (WT) or mutant with a single-nucleotide mutation (m1). Further, the PCR products determined to be WT or m1 based on the result were cloned into pBluescript II at the EcoRV site. The nucleotide sequence was determined to confirm the nucleotide sequence at the site of SNPs. The wild-type nucleotide sequence is shown in SEQ ID NO: 5. In m1, the residue at nucleotide 111 in SEQ ID NO: 5 was not G but A (FIG. 7).

Then, the primers designed to discriminate WT and m1 of human CYP2C19 according to the present invention comprise the following nucleotide sequences. The positions of the respective primers in the target nucleotide sequence are shown in FIG. 7. The 5'-end of FA contains the site of mutation to be detected. Thus, when the predicted nucleotide sequence is not contained in the region of the target nucleotide sequence, the reaction of complementary strand synthesis is inhibited.

RA(R1+R2)/SEQ ID NO: 1

5'-GGGAACCCATAACAAATTACTTAAAAAC-CTGTGTTCTTTTACTTTCTCCAAAATATC-3'

Outer primer R3/SEQ ID NO: 2

5'-AGGGTTGTTGATGTCCATC-3'

FA(F1+F2)/SEQ ID NO: 3

5'-CGGGAAATAATCAATGATAGTGG-GAAAATATGCTTTTAATTTAATAAAT-TATTGTTTTCTCTTA G-3'

Outer primer F3/SEQ ID NO: 4

5'-CCAGAGCTTGGCATATTGTATC-3'

Incubation was carried out at 60° C. for 2 hours using the primers, that comprise the above nucleotide sequences, and $10^{-19}$ mol/tube (about 60000 molecules) of pBluescript II (linearized with EcoRI) wherein WT or m1 had been inserted as the template. The reaction was carried out remaining the template double-stranded. The composition of the reaction solution was as follows:

The composition of reaction solution (in 25 μL)
20 mM Tris-HCl pH 8.8
10 mM KCl.
10 mM $(NH_4)_2SO_4$
4 mM $MgSO_4$
1 M Betaine
0.1% Triton X-100
0.4 mM dNTP
8 U Bst DNA polymerase (NEW ENGLAND BioLabs)

Primers:
1600 nM FA
1600 nM RA
200 nM F3
200 nM R3

Figure 8:
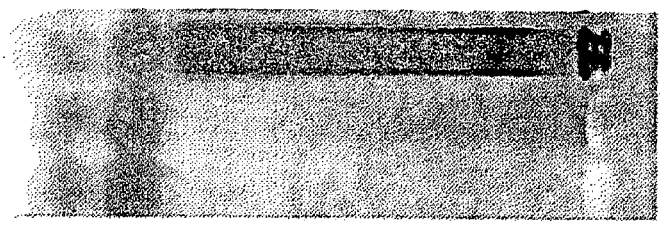
FIG. 8 depicts a photograph demonstrating the result of the mutation detection method of the present invention. Each lane represents: target template (the specific region has the predicted nucleotide sequence); template with a single-nucleotide mismatch (the specific region has a nucleotide sequence with a single nucleotide difference to the predicted nucleotide sequence); and no template (primer alone used as a control).

5 μL of loading buffer was added to 5 μL of the above reaction solution, and then, was loaded onto a 2% agarose gel (0.5% TBE). Electrophoresis was carried out for 0.5 hour at 100 V. After electrophoresis, the gel was stained with ethidium bromide (EtBr) to visualize the nucleic acids. The result is depicted in FIG. 8. No amplification could be observed when the reaction contained no template or the template m1 which contains a single-nucleotide mismatch. However, amplification products were detected when WT was used as the template. Thus, it was verified that unambiguous discrimination of single-nucleotide differences is enabled according to the present invention.

Example 2

Detection of Mutations in the Human CYP2C19 Gene (2)

The mutation detection method of the present invention was performed using the same primers as those used in Example 1. The composition of the reaction solution was the same as that used in Example 1 except for $10^{-21}$ mol/tube (about 600 molecules) of pBluescript II (linearized with EcoRI) wherein WT or m1 had been inserted was used as the target nucleotide sequence. Incubation was carried out at 64°

C. EtBr is added at a final concentration of 0.25 µg/ml to the reaction solution. The reaction was monitored for 6 hours with ABI Prism 7700 (Perkin Elmer).

Figure 9:
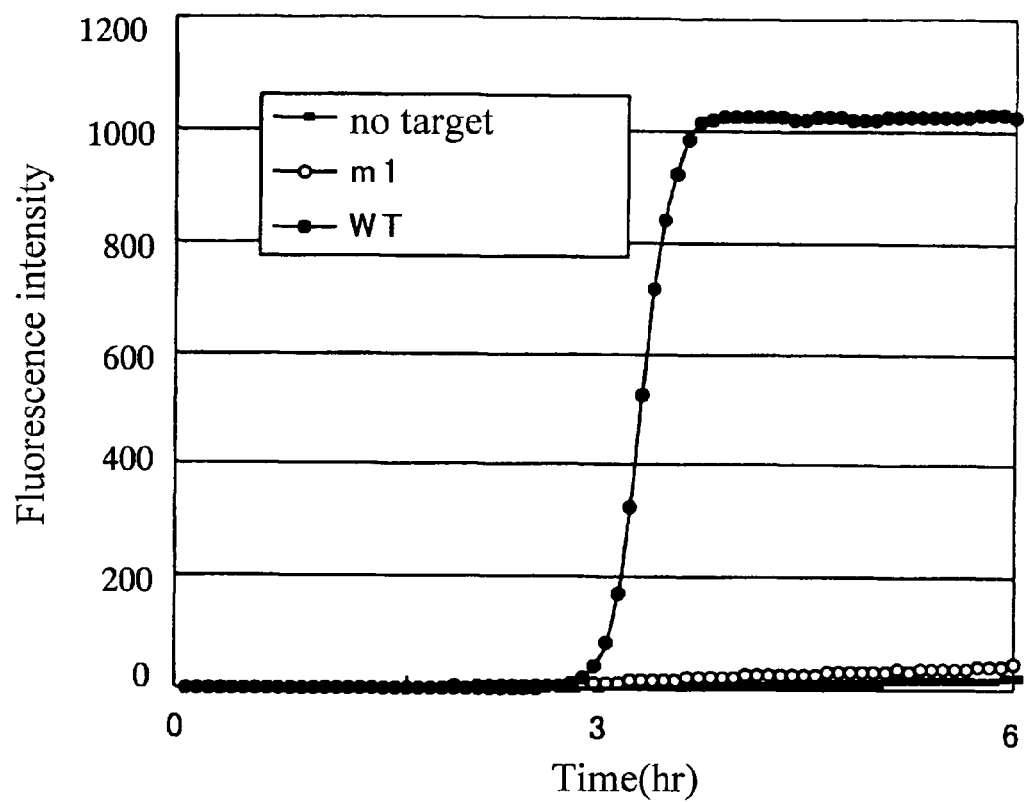
FIG. 9 depicts a graph demonstrating the result obtained by the mutation detection method of the present invention. Herein, the ordinate indicates the fluorescence intensity and the abscissa the reaction time (hour). –■–: no target; –○–: m1; and –●–: WT.

The result is demonstrated in FIG. 9. No amplification could be detected during 6-hours of reaction when no template or the template m1, that contains a single-nucleotide mismatch, was used in the reaction. When WT was used as the template, the fluorescence intensity enhanced with the progress of the amplification reaction. It was verified that unambiguous discrimination of single-nucleotide differences in the specific region can be achieved according to the present invention. Further, it was demonstrated that the mutation detection method based on the present invention can be conducted isothermally, and in addition, the reaction could be monitored with a conventional device for fluorescence assay.

The ABI Prism 7700 used in the Example is originally a device for monitoring PCR. However, thermal cycling as in PCR was not required in the detection method of the present invention; the reaction was achieved only by isothermal incubation (64° C.). Thus, the mutation detection method according to this Example can be performed in a device for fluorescence assay with an incubator.

Example 3

Detection of Mutations in the Human CYP2C19 Gene (3)

Figure 10:
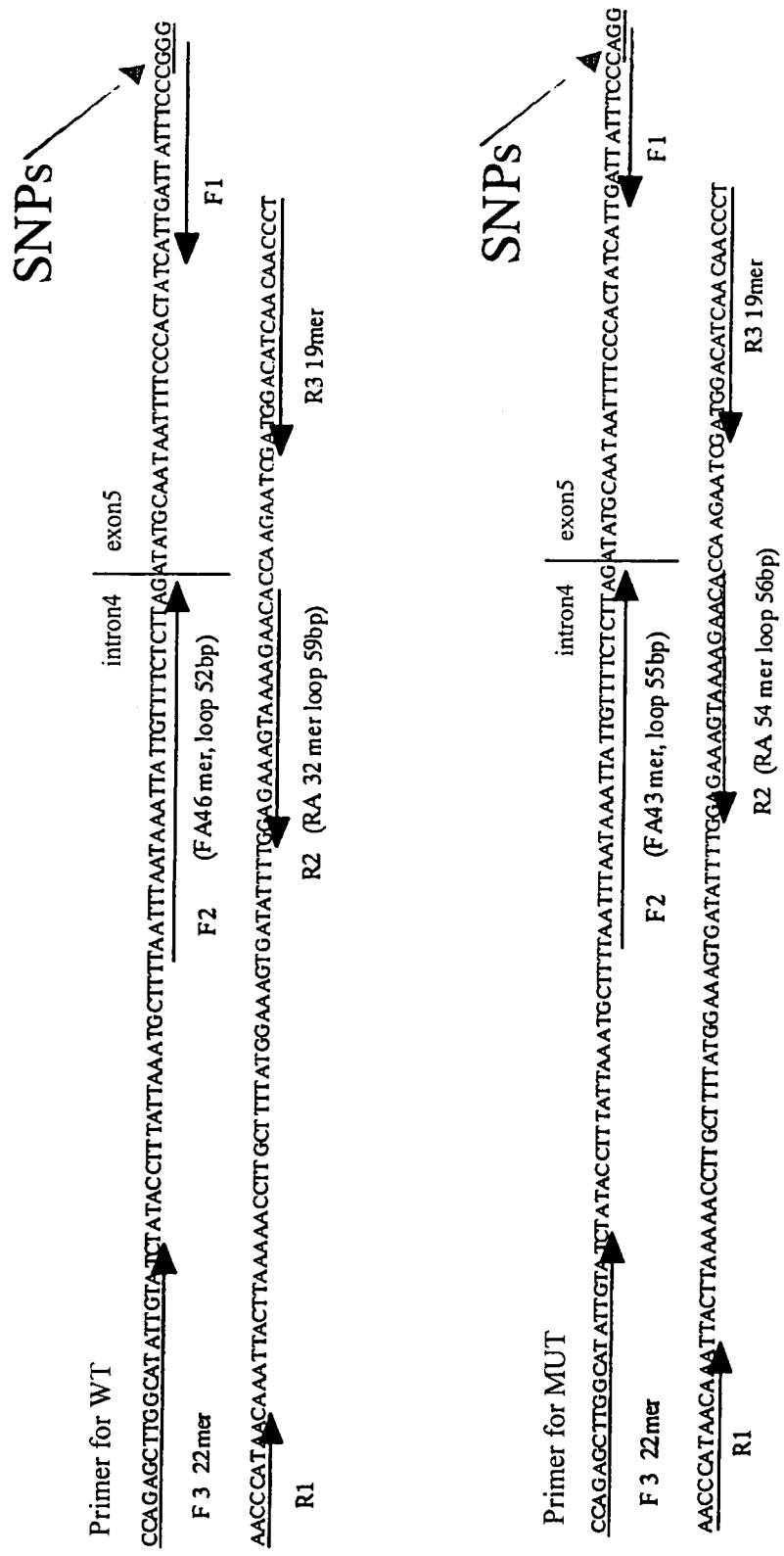
FIG. 10 depicts schematic illustrations demonstrating the target nucleotide sequences, that were used in the detection of SNPs in Example 3, and the positional relation of primers to the target nucleotide sequences.

The following experiment was carried out to assess the specificity of the method for detecting nucleotide sequence mutations of the present invention. More specifically, primers corresponding to the mutant-type and wild-type predicted nucleotide sequences in the specific region were designed respectively, and the mutation detection method of the present invention was conducted using the primers. The nucleotide sequences of the primers prepared are listed below. The experiment was carried out by the same procedure as in Examples 1 and 2 using human CYP2C19 gene as the template and the primer set, which amplifies sequences with the mutation of interest (MUT) (the mutant-type predicted nucleotide sequence), and the primer set, that amplifies sequences of the wild type (WT) (the wild-type predicted nucleotide sequence). Positions of respective primers in the target nucleotide sequence are demonstrated in FIG. 10. The second nucleotide from the 5'-ends of FA and RA corresponds to the site of SNPs.

A set of primers to detect the wild type

FA(F1+F2)/SEQ ID NO: 6:

5'-CCGGGAAATAATCAATGTAATT-TAATAAATTATTGTTTTCTCTTAG-3'

RA(R1+R2)/SEQ ID NO: 7:

5'-CGGGAACCCATAACTGTTCTTTTACTTTCTCC-3'

A set of primers to detect the mutation

FA(F1+F2)/SEQ ID NO: 8:

5'-CAGGAACCCATAACAAATTACTTAGTGT-TCTTTTACTTTCTC-3'

RA(R1+R2)/SEQ ID NO: 9:

5'-CAGGAACCCATAACAAATGTGTTCTTT-TACTTTCTCC-3'

The outer primers, R3 and F3, used in this Example consist of the nucleotide sequences of SEQ ID NO: 2 and SEQ ID NO: 4, respectively (the same as in Example 1).

A solution was prepared, which contained the primers comprising the above nucleotide sequences and 6,000 molecules/tube of pBluescript II (linearinzed with EcoRI), in which WT or m1 had been inserted, as the template. The solution was heated at 95° C. for 3 minutes, and combined with the following reaction solution. The total volume was 25 µL. The mixture was incubated at 60° C. for 3 hours. The composition of reaction solution was as follows.

The composition of reaction solution (in 25 µL)
20 mM Tris-HCl pH 8.8
10 mM $(NH_4)_2SO_4$
10 mM KCl
3.5 mM $MgSO_4$
1 M Betaine
0.1% Triton X-100
0.4 mM dNTPs
8 U Bst DNA polymerase
1600 nM FA
1600 nM RA
200 nM F3
200 nM R3

EtBr was added at a final concentration of 0.25 µg/ml to the reaction solution. The reaction was monitored for 3 hours with ABI Prism 7700 (Perkin Elmer).

Figure 11:
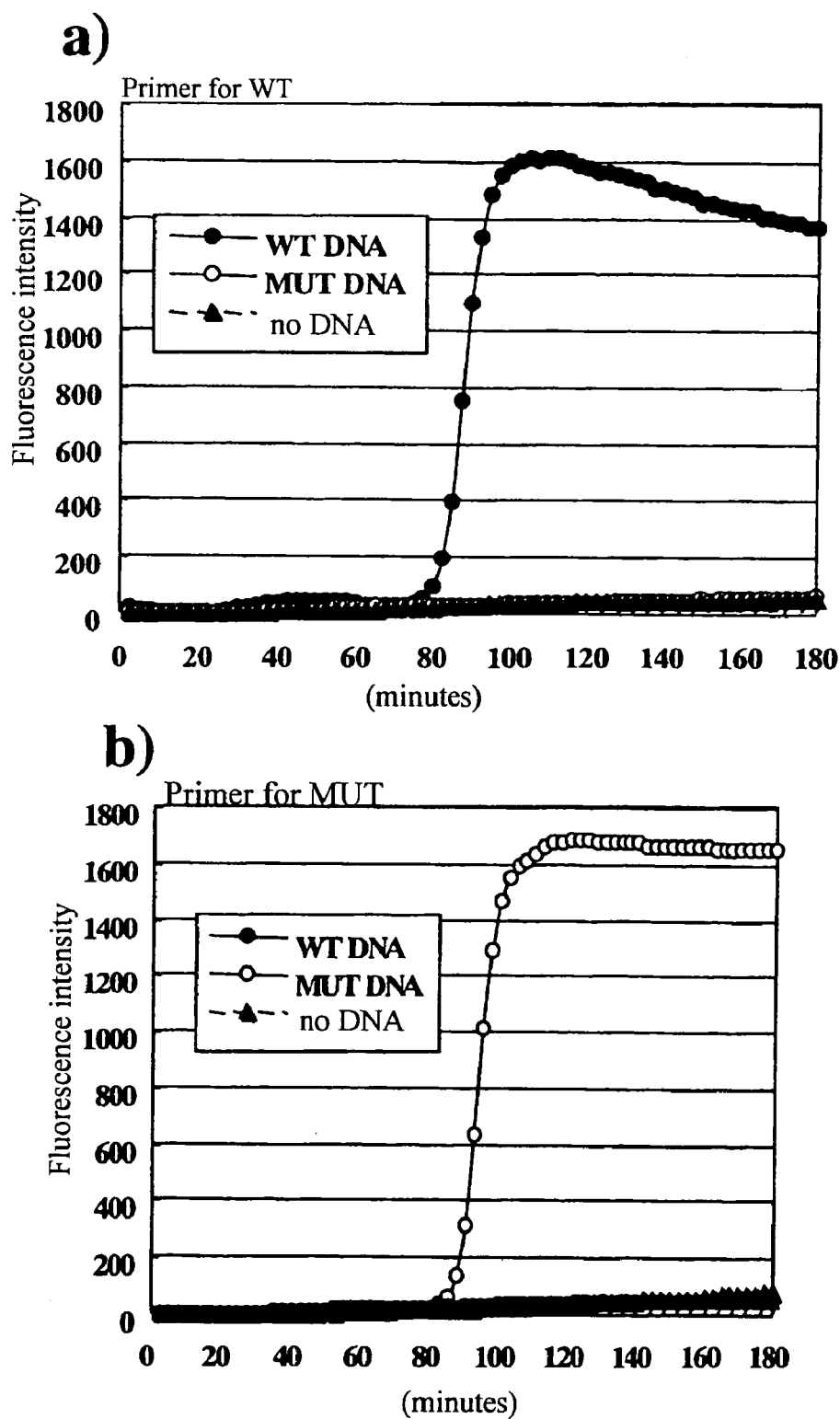
FIG. 11 depicts graphs demonstrating the results of the mutation detection method of the present invention. Panel a) and b), respectively, demonstrates the result obtained by reacting the primer set for wild type (WT) and the primer set for mutant (MUT) with respective template DNAs. Herein, the ordinate indicates the fluorescence intensity and the abscissa the reaction time (minute). –●–: wild type (WT); –○–: mutant (MUT); and —▲—: no DNA.
Figure 12:
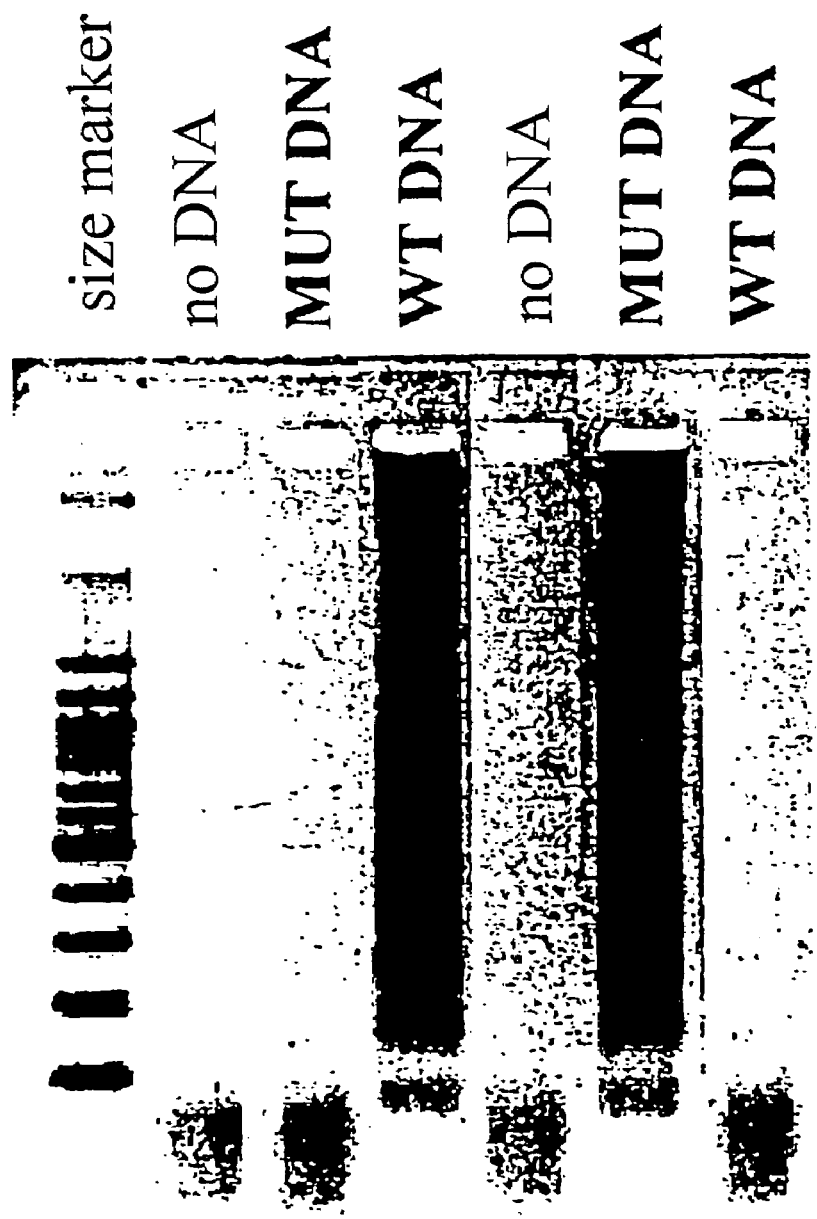
FIG. 12 depicts a photograph demonstrating the result of the mutation detection method of the present invention. Each lane represents: products obtained by reacting respective template DNAs with the wild-type (WT) primer set and the mutant-type (MUT) primer set. No DNA (without template DNA); MUT DNA (the mutant CYP2C19 gene as the template); and WT DNA (the wild-type CYP2C19 gene as the template).

The result is shown in FIG. 11. Further, 5 µL of the above-mentioned reaction solution was subjected to electrophoresis using the same procedure as used in Example 1 after the reaction was completed; the result is shown in FIG. 12. It was verified that the amplification with the wild-type primer set or the mutant primer set proceeded during the reaction for 3 hours only when the template had the predicted nucleotide sequence. Even when the experiment was carried out with only 6,000 template molecules, the amplification reaction reached the plateau in about 100 minutes. Thus, it was demonstrated that the detection method of the present invention is highly sensitive. 6,000 DNA molecules correspond just to the number of copies of genome DNA derived from white blood cells in 1 µL of blood. The number of white blood cells in an adult person in the normal condition has been estimated to be 4,000 to 8,000 cells. Thus, the average number of white blood cells is 6,000. Since the majority of blood DNA is derived from white blood cells, the number of white blood cells corresponds to the number of DNA copies in blood. Accordingly, if analysis results are obtainable with 6,000 DNA molecules, the gene analysis can be achieved with 1 µL of blood sample.

On the other hand, when the nucleotide sequence of the template was identical to neither of the predicted nucleotide sequences, there was no detectable amplification with the primer set for either the wild type or mutant during the reaction for 3 hours. Thus, it was demonstrated that, even with a small quantity of sample, the mutation detection method of the present invention achieves a highly reliable checking-mechanism for nucleotide sequences.

Example 4

Specificity Against the Human p450CYP2C19 Gene

The specificity of the method for detecting mutations according to the present invention was assessed by an experiment using a 100 times larger quantity of a template consisting of a nucleotide sequence similar to that of the template to be detected for mutation. The same template as in Example 3, human p450CYP2C19 gene, was used to detect for mutations. Human p450CYP2C9 gene and human p450CYP2C18 gene was used as the templates consisting of nucleotide sequences similar to that of the gene. These genes were also cloned into pBluescript II and the nucleotide sequences were verified by the same procedure as in Example 1. Then, the genes were used in this experiment.

600,000 molecules/tube of the human p450CYP2C9 gene or human p450CYP2C18 gene were used instead of 6,000 molecules/tube of the human p450CYP2C19 as the templates in this experiment. Other experimental conditions were the same as those in Example 3.

Figure 13:
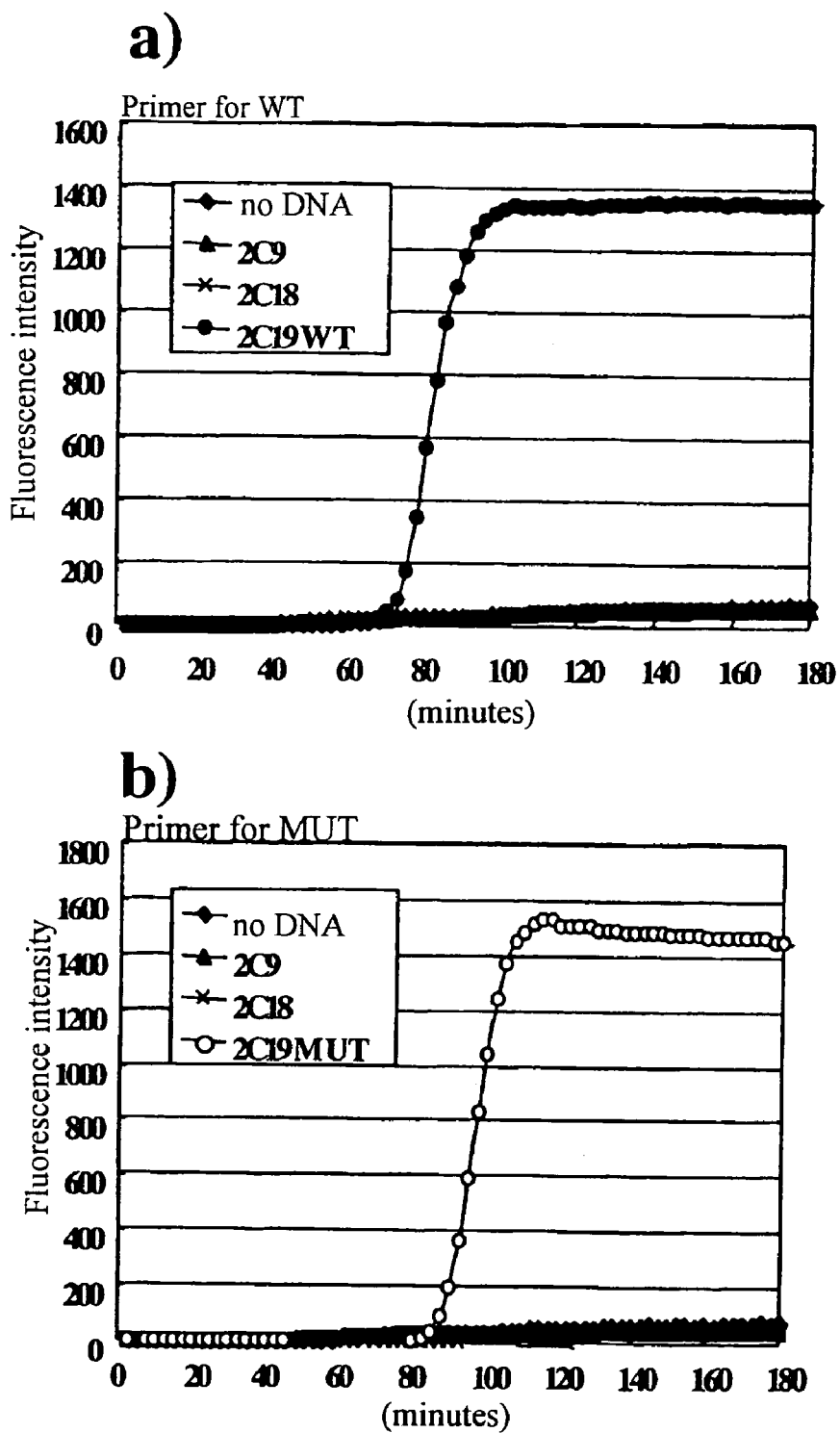
FIG. 13 depicts graphs demonstrating the specificity of the mutation detection method of the present invention. Panel a) and b), respectively, demonstrates the results obtained by reacting the primer set for wild type (WT) and that for mutant (MUT) with respective template DNAs. Herein, the ordinate indicates the fluorescence intensity and the abscissa the reaction time (minute). —♦—: no DNA; —▲—: CYP2C9 gene; —✕—: CYP2C18 gene; –●–: wild type (WT) CYP2C19; and –○–: mutant (MUT) CYP2C19.

The result is shown in FIG. 13. With the primer set for wild type, amplification was detectable when the template was 6,000 molecules of CYP2C19WT DNA. However, when the template was 600,000 molecules of the CYP2C9 or CYP2C18 gene, there was no detectable amplification with the same primer set. Likewise, with the primer set for the mutant, amplification was detectable when the template was 6,000 molecules of CYP2C19MUT DNA, but there was no detectable amplification with the same primer set when the template was 600,000 molecules of the CYP2C9 or CYP2C18 gene. The result shown above indicates that, according to the mutation detection method of the present invention, a nucleotide sequence of interest can be discriminated from other similar nucleotide sequences in a group of genes comprising nucleotide sequences similar to one another, and the mutation was also unambiguously detectable.

Figure 6:
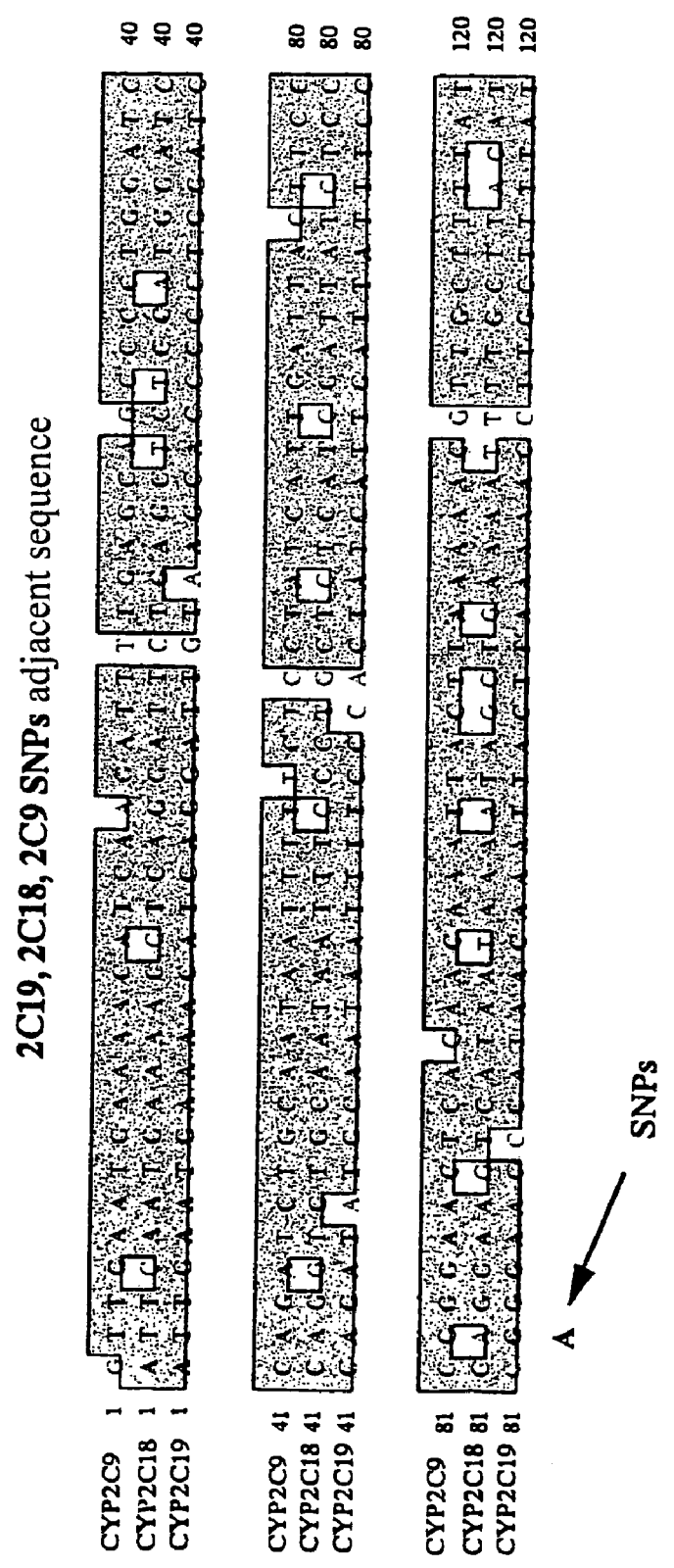

As seen in FIG. 6, the nucleotide sequences of p450CYP2C19, p450CYP2C9, and p450CYP2C18 are very similar to one another. According to conventional methods for detecting nucleotide sequences, it had been nearly impossible to discriminate nucleotide sequences with such high similarity and detect mutations at the same.

Example 5

Assay with the Loop Primer (1)

-Detection of SNPs in the Human p450CYP2C19 Gene-

The following experiments were carried out in order to verify that the improving effect of the loop primer, invented by the applicants (filed 19, Sep., 2000; Japanese Patent Application No. 2000-283862), on the efficiency of the LAMP method applies also to the mutation detection method of the present invention.

Figure 14:
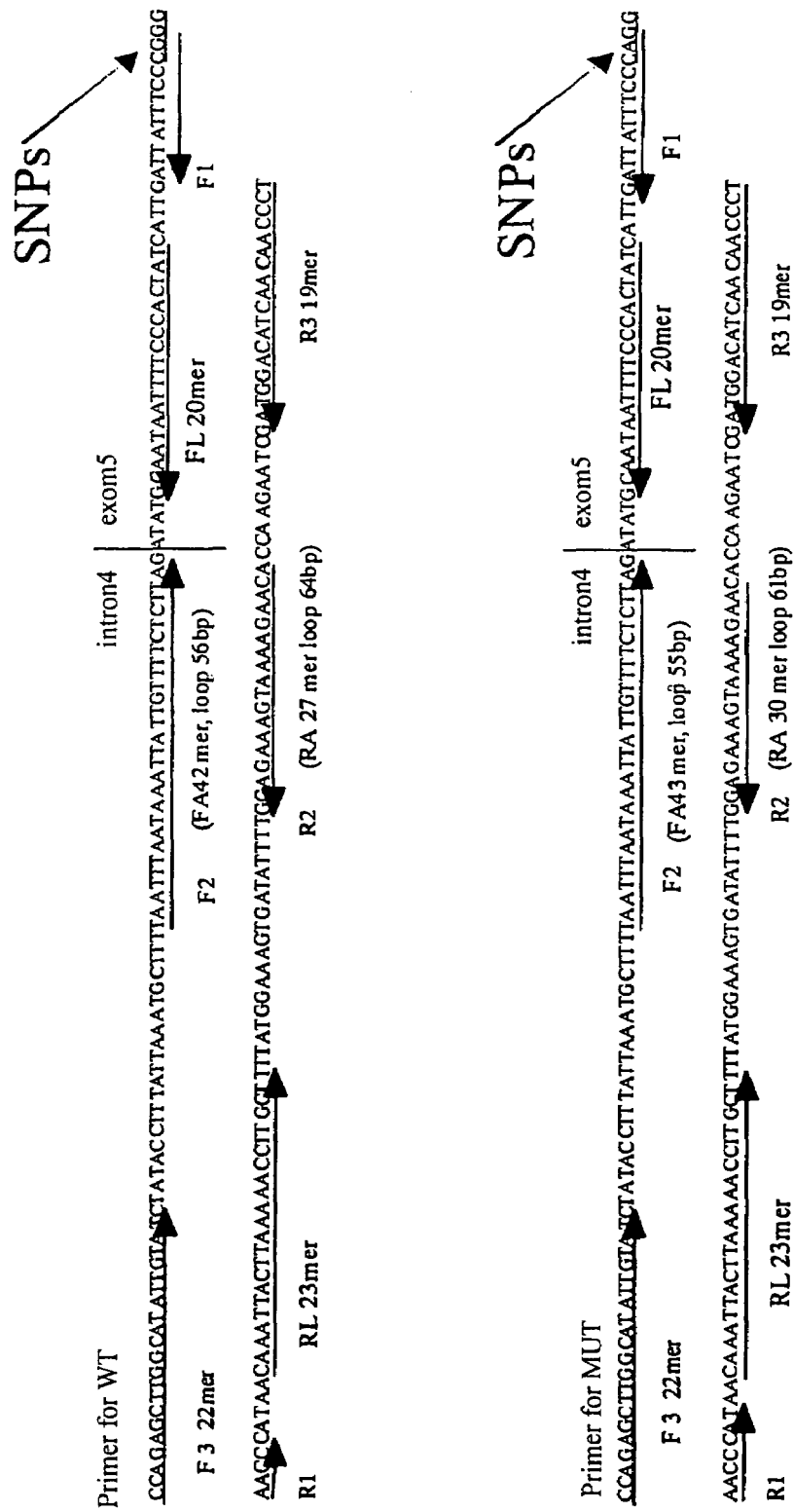
FIG. 14 depicts a schematic illustration of the target nucleotide sequence, that was used in the detection of SNPs is Example 5, and the positional relation of primers to the target nucleotide sequence.

First, primers and loop primers comprising the nucleotide sequences shown below were designed. A loop primer refers to a primer that serves as an origin of a complementary strand synthesis existing between F2 and F1 on the elongation products from FA. Likewise for RA, a primer that serves as a complementary strand synthesis origin existing between R2 and R1 on the above-mentioned elongation products from RA is used as the loop primer. Specifically, the loop primers used comprise the nucleotide sequences shown below. The loop primers can be used in combination with the wild-type (WT) primer set or in combination with the mutant-type (MUT) primer set. The positions of respective primers in the target nucleotide sequence, which were used in the reaction, are shown in FIG. 14. As in Example 3, the second nucleotide from the 5'-ends of FA and RA corresponds to the site of SNPs.

A set of primers to detect the wild type

FA(F1+F2)/SEQ ID NO: 10:

5'-CCGGGAAATAATCTAATTTAATAAAT-TATTGTTTTCTCTTAG-3'

RA(R1+R2)/SEQ ID NO: 11:

5'-CGGGAACCCTGTTCTTTTACTTTCTCC-3'

A set of primers to detect the mutant

FA(F1+F2)/SEQ ID NO: 12:

5'-CTGGGAAATAATCATAATTTAATAAAT-TATTGTTTTCTCTTAG-3'

RA(R1+R2)/SEQ ID NO: 13:

5'-CAGGAACCCATATGTTCTTTTACTTTCTCC-3'

Loop primer FL/SEQ ID NO: 14:

5'-GATAGTGGGAAAATTATTGC-3'

Loop primer RL/SEQ ID NO: 15:

5, —CAAATTACTTAAAAACCTTGCTT-3'.

The outer primer R3 consists of the nucleotide sequence of SEQ ID NO: 2, and the outer primer F3 consists of the nucleotide sequence of SEQ ID NO: 4 (the same as in Example 1).

A solution comprising either of the above primer sets and the loop primers as well as 6,000 molecules/tube of pBluescript II (linearized with EcoRI), in which WT or m1 had been inserted, as the template was heated at 95° C. for 3 minutes, and combined with the following reaction solution to a total volume of 25 μL. The mixture was incubated at 60° C. for 3 hours. The composition of the reaction solution was as follows.

The composition of reaction solution (in 25 μL):
    20 mM Tris-HCl pH 8.8
    10 mM $(NH_4)_2SO_4$
    10 mM KCl
    4.0 mM $MgSO_4$
    1 M Betaine
    0.1% Triton X-100
    0.5 mM dNTPs
    8 U Bst DNA polymerase
    1600 nM FA
    1600 nM RA
    200 nM F3
    200 nM R3
    800 nM FL
    800 nM RL, and
    6000 molecules/tube of template DNA.

EtBr was added at a final concentration of 0.25 μg/ml to the reaction solution. The reaction was monitored for 1 hour with ABI Prism 7700 (Perkin Elmer). The result is demonstrated in FIG. 15.

Figure 15:
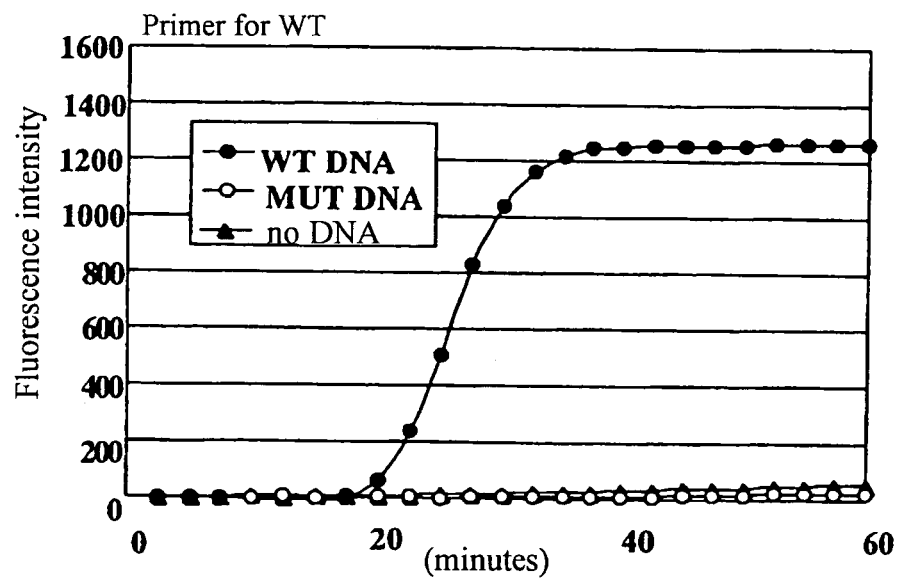
FIG. 15 depicts graphs demonstrating the result of the mutation detection method of the present invention using the loop primers. Panel a) and b), respectively, demonstrate the results obtained, by reacting the primer set for wild type (WT) and that for mutant (MUT) with respective template DNAs. Herein, the ordinate indicates the fluorescence intensity and the abscissa the reaction time (minute). - -: wild type (WT); –○–: mutant (MUT); and —▲—: no DNA.
Figure 15:
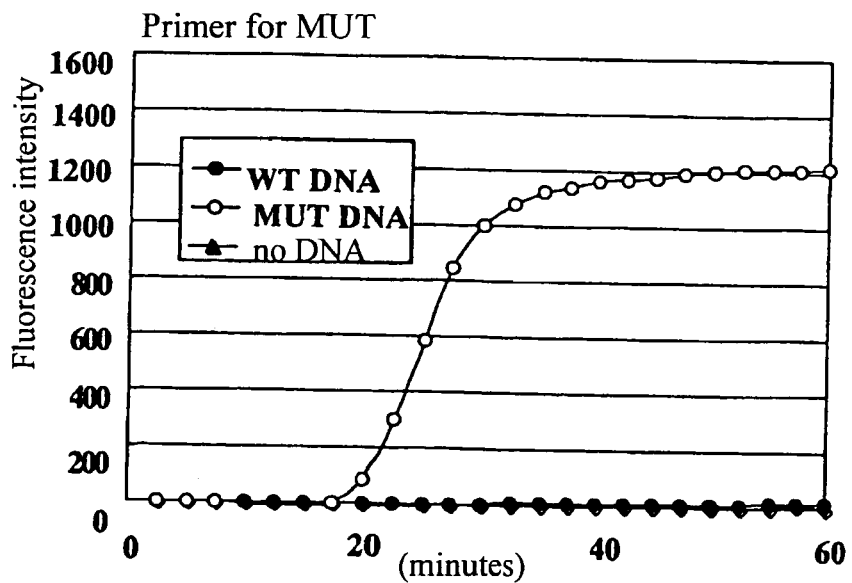

Increased fluorescence signal due to the amplified products were observed about 70 minutes and about 80 minutes after the start of reaction with the WT-type primer set and the MUT-type primer set, respectively, in the reaction without the loop primer (FIG. 11). Whereas increased fluorescence signal due to the amplified products were detected about 20 minutes after the start of reaction with each primer set, wild-type or mutant-type, in the reaction with the loop primers (FIG. 15). The reaction rate was shown to increase by the use of the loop primers.

On the other hand, in the detection of SNPs, it was confirmed that the amplification reaction proceeded by discriminating single-nucleotide differences regardless of the use of the loop primers. Thus, it was demonstrated that the use of the loop primers contribute to great improvement of the reaction rate without sacrificing the specificity.

Example 6

Assay with the Loop Primer (2)

-Assessment of Specificity Against the Human p450CYP2C19 Gene-

The specificity of the method for detecting mutations according to the present invention was assessed by an experiment using the loop primers and templates comprising nucleotide sequences similar to that of the template to be detected for mutations with an amount 100 times larger than that was used for detecting the mutation. 600,000 molecules/tube each of human p450CYP2C9 gene and human p450CYP2C18 gene instead of 6,000 molecules/tube of human p450CYP2C19 were used as the templates in this experiment. Other reaction conditions were the same as in Example 5.

Figure 16:
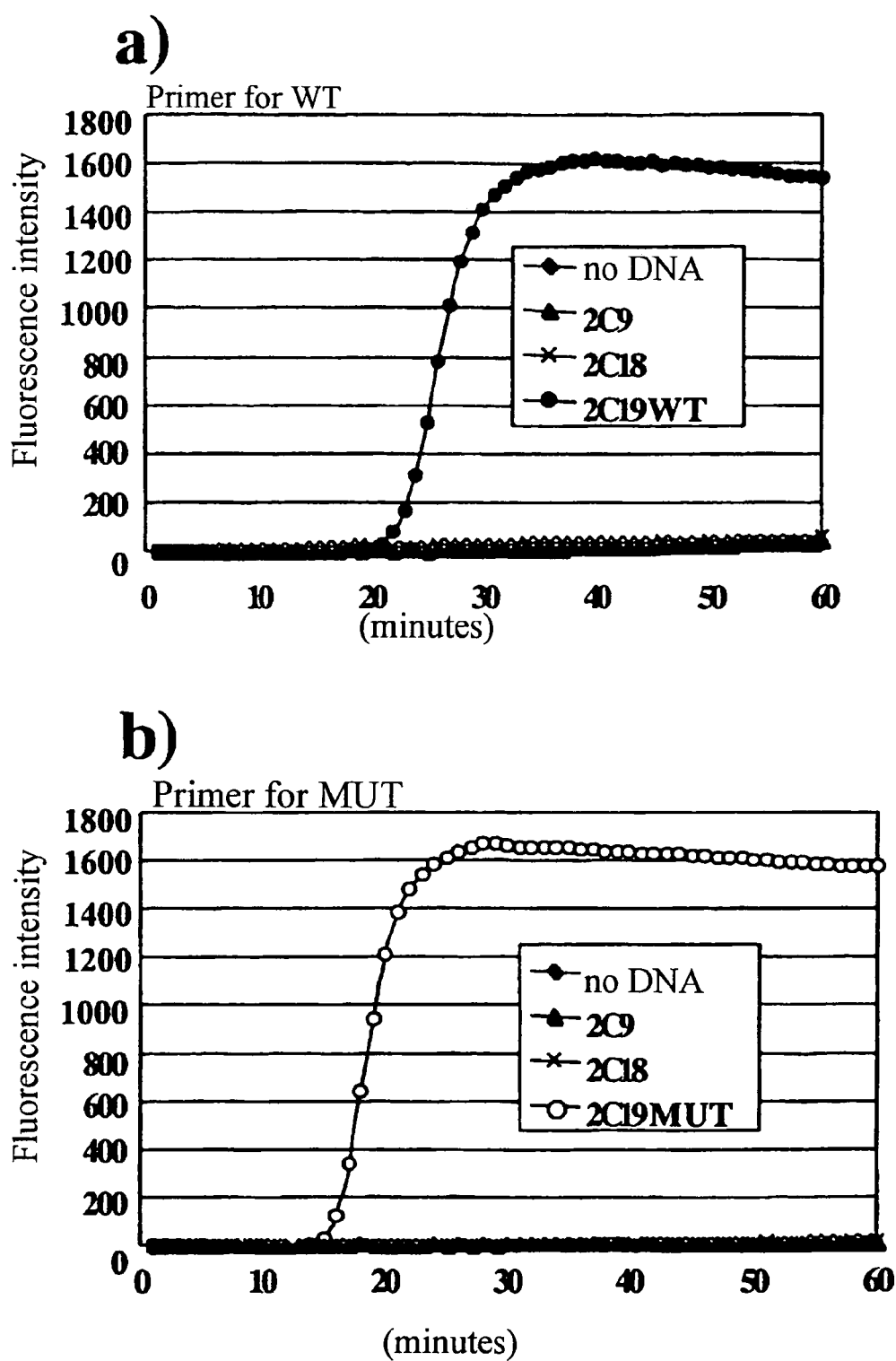
FIG. 16 depicts graphs demonstrating the specificity of the mutation detection method of the present invention using the loop primer. Panel a) and b), respectively, demonstrate the results obtained by reacting the primer set for wild type (WT) and that for mutant (MUT) with respective template DNAs. Herein, the ordinate indicates the fluorescence intensity and the abscissa the reaction time (minute). —♦—: no DNA; —▲—: CYP2C9 gene; —✕—: CYP2C18 gene; –●–: wild type (WT) CYP2C19; and –○–: mutant (MUT) CYP2C19.

The result is shown in FIG. 16. With the primer set for the wild type, amplification was detectable when 6,000 molecules of CYP2C19WT DNA were used as the templates. However, when 600,000 molecules of the CYP2C9 or CYP2C18 gene were used as the templates, no detectable amplification could be observed with the same primer set. Likewise, with the primer set for mutant, amplification was detectable only when 6,000 molecules of CYP2C19MUT DNA were used as the templates, but not when 600,000 molecules of the CYP2C9 or CYP2C18 gene were used as the templates. Therefore, the mutation detection method of the present invention distinguishes the object nucleotide sequence from a similar nucleotide sequences which exist in a group of genes comprising nucleotide sequences similar to one another, and unambiguously detects object mutations even when a loop primer is utilized in the method.

Example 7

Assay with Blood Samples

DNA was extracted from blood samples collected from volunteers (35 samples) with QIAamp DNA Blood Kit (Qiagen). The m1 region of the human p450CYP2C19 gene was amplified from the extracted DNA by PCR using the primer sequences indicated in Unexamined Published Japanese Patent Application (JP-A) No. Hei 10-14585. The amplification was carried out with Z-Taq polymerase (Takara Shuzo) according to the protocol for Z-Taq.

The obtained PCR products were analyzed by PCR-RFLP. The procedure was as follows. First, 3 µL of the PCR products was digested with restriction enzyme MspI at 37° C. for 3 hours, and electrophoresed on a 4% agarose gel (Amplisize Agarose, BIO-RAD). After electrophoresis, the gel was stained with SYBR Green I (FMC), and the band pattern for the DNA was observed for typing the m1 region.

Three samples of each of wild type homozygote (WT/WT), wild type/mutant heterozygote (WT/MUT), and mutant homozygote (MUT/MUT), 9 samples in total among all the samples were analyzed for the m1 region by the mutation detection method of the present invention. The nucleotide sequences of the PCR products from the used 9 samples were determined to confirm the results obtained by the typing using PCR-RFLP. The mutation detection method of the present invention was performed according to the protocol described in Example 5. The sample DNA was used at an amount which is theoretically equivalent to that extracted from 1 µL of blood. Specifically, a $\frac{1}{7,000}$ aliquot of DNA extracted from 7 ml of blood was used as the sample DNA.

Figure 17:
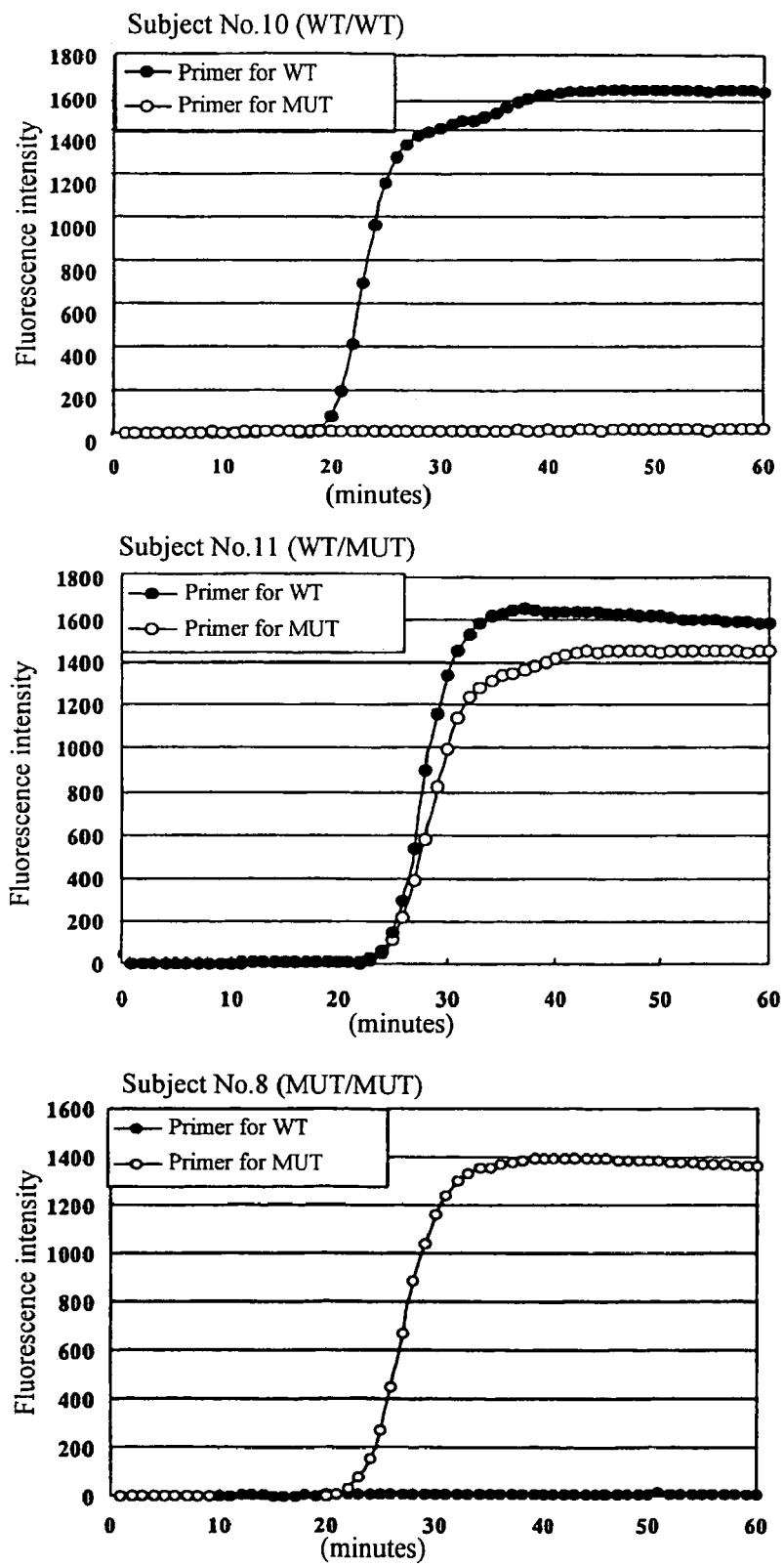
FIG. 17 depicts graphs demonstrating the result detecting mutations in blood samples by the mutation detection method of the present invention using the loop primer. Sample No. 10: a homozygote of wild type (WT/WT); sample No. 11: a heterozygote of wild type/mutant (WT/MUT); and sample No. 8: a homozygote of mutant (MUT/MUT). Herein, the ordinate indicates the fluorescence intensity and the abscissa the reaction time (minute). –●–: wild-type (WT) primer; and –○–: mutant-type (MUT) primer.

With respect to all the 9 samples, the results obtained by the mutation detection method of the present invention agreed with those obtained by PCR-RFLP. The results of the reaction with sample No. 10 (the result of WT/WT by PCR-RFLP), sample No. 11 (the result of WT/MUT by PCR-RFLP), and sample No. 8 (the result of MUT/MUT by PCR-RFLP) of the nine are shown in FIG. 17.

The amplification reaction on the sample of wild type homozygote (WT/WT) occurred only when the wild-type (WT) primer set was used, and no amplification could be detected with the primers for mutant (MUT). On the other hand, genes were amplified with both primer sets, primer set for wild type (WT) and that for mutant (MUT), where the sample was heterozygote (WT/MUT). Further, amplification of the sample of mutant homozygote (MUT/MUT) occurred only with the mutant-type (MUT) primers, and not with the wild type (WT) primers. This indicates that homozygote/heterozygote can be conveniently assessed based on a matrix as shown below from the result of reaction by the combined use of primer sets for the wild type and mutant.

|  | Wild type | Mutant |
| --- | --- | --- |
| Wild type homozygote | + | − |
| Mutant homozygote | − | + |
| Heterozygote | + | − |

Further, the amplified nucleic acid was confirmed by sequencing to have the nucleotide sequence of the CYP2C19 gene. A blood-derived DNA sample contains many similar sequences, such as CYP2C9 and CYP2C18, beside the CYP2C19 gene. Only the CYP2C19 gene, which was the target gene, was specifically amplified even in the presence of such similar sequences, and the detection of single-nucleotide differences was achieved in a single-round amplification reaction. Thus, it was confirmed that SNP typing of a gene, for which many genes with similar sequences exist, can be conducted just by testing the presence or absence of amplification products in a single-round amplification reaction.

INDUSTRIAL APPLICABILITY

According to the present invention, a target nucleotide sequence can be accurately assessed, whether it differs from a predicted nucleotide sequence or not. The method of the present invention is useful in analyzing mutations and polymorphisms within nucleic acids. This method is based on a simple enzymatic reaction. Thus, the method can be performed without any special devices or reaction components, which enables the method to be readily conducted at a low cost.

Further, since the method for detecting mutations and polymorphisms of the present invention comprises a reaction containing amplification of the target nucleotide sequence, differences in nucleotide sequences can be discriminated using the amount of the amplified nucleic acid product as an index. This allows highly sensitive and reproducible nucleotide sequence analyses. In addition, the complementary strand synthesis based on the principle of reaction used in the present invention, proceeds after checking the target nucleotide sequence at the start of every round. Therefore, even when a wrong complementary strand is erroneously synthesized, such erroneous reaction never influences the ultimate result of analysis. According to PCR, a conventional gene amplification method, once a wrong complementary strand is synthesized, it is impossible to accurately assess the result. Thus, PCR is actually not applicable to this type of analysis. Certain errors are inevitable in all kinds of nucleotide sequence checking-mechanisms based on primer hybridization. High S/N ratios, minimizing the influence of errors in complementary strand synthesis of nucleic acids, and at the same time accumulating in large quantity the correct reaction product without any errors has been achieved according to the present invention.

Thus, the present invention is a pioneering invention, establishing for the first time a method for discriminating nucleotide sequences based on a nucleic acid amplification reaction.

Further, the feature of the present invention, that the process of over all reaction is controlled in multiple regions, is advantageous in the detection of minor differences in nucleotide sequences in the presence of multiple genes with similar nucleotide sequences. Because of this feature, typing of HLA and platelet alloantigen or pathogenic microorganisms can be accurately and conveniently conducted according to the present invention. Furthermore, the detection of SNPs involved in the activity of enzymes associated with drug metabolism can be also conveniently achieved according to the present invention.

The invention claimed is:

1. A method for detecting mutations and/or polymorphisms within a specific region of a target nucleotide sequence comprising the steps of:
   (1) incubating the following elements (a) to (e) under conditions that allow complementary strand synthesis wherein second and first primers are used as origins:
       (a) a nucleic acid sample comprising a target nucleotide sequence;
       (b) a DNA polymerase catalyzing complementary strand synthesis which includes strand displacement;
       (c) a second primer, wherein the 3'-end of the second primer anneals to the 3'-side region of one strand of said target nucleotide sequence and the 5'-side of the second primer includes a nucleotide sequence complementary to the predicted nucleotide sequence that constitutes a region on the products of the complementary strand synthesis reaction that uses the second primer as the origin;

(d) a first primer, wherein the 3'-end of the first primer anneals to the 3'-side region of the other strand of said target nucleotide sequence, and the 5'-side of the first primer includes a nucleotide sequence complementary to the predicted nucleotide sequence that constitutes a region on the products of the complementary strand synthesis reaction that uses the first primer as the origin; and (e) nucleotide substrates; and (2) correlating the amount of product synthesized by a complementary strand synthesis reaction, which uses the target nucleotide sequence as the template, with the presence of a mutation and/or polymorphism in the specific region, wherein a nucleotide sequence arranged on at least one of the 5'-ends of the second and first primer contains a nucleotide sequence that is complementary to the predicted nucleotide sequence of said specific region or the complementary strand thereof, and wherein the complementary strand, that is synthesized using the nucleotide sequence arranged on the 5'-end as the template and functions as the origin of complementary strand synthesis by annealing to the specific region or the complementary strand thereof, inhibits the complementary strand synthesis when the nucleotide sequence that contains the specific region is not a predicted one.

2. The method of claim 1, wherein both of the nucleotide sequences arranged on the 5'-end of the second primer or first primer contain a nucleotide sequence that is complementary to the predicted nucleotide sequence of said specific region or the complementary strand thereof, and wherein the complementary strand, that is synthesized using the nucleotide sequence arranged on the 5'-end as the template and functions as the origin of complementary strand synthesis by annealing to the specific region or the complementary strand thereof, inhibits the complementary strand synthesis when the nucleotide sequence that contains the specific region is not a predicted one.

3. The method of claim 1, additionally comprising the following elements:

(f) a third primer, wherein the third primer serves as the origin of the complementary strand synthesis reaction, further wherein the 3'-side of the annealing region of the first primer on the template functions as the origin; and, (g) a fourth primer, wherein the fourth primer serves as the origin of the complementary strand synthesis reaction, further wherein the 3'-side of the annealing region of the second primer on the template functions as the origin.

4. The method of claim 1, wherein a gene comprising a nucleotide sequence similar to the nucleotide sequence of the target nucleotide sequence is present in the same sample.

5. The method of claim 4, wherein the gene is a family gene and/or a pseudogene.

6. The method of claim 5, wherein the family gene and/or the pseudogene is any gene selected from the group consisting of the cytochrome P450 family, human leukocyte histocompatibility antigens, and platelet alloantigens.

7. The method of claim 1, wherein the polymorphism is a single nucleotide polymorphism.

8. The method of claim 1, wherein the target nucleotide sequence is selected from the nucleotide sequences of genes from any pathogenic virus or pathogenic microorganism selected from the group consisting of hepatitis C virus, influenza virus, malaria, and *Helicobacter pylori*.

9. The method of claim 1, wherein the incubation of step (1) is performed in the presence of a melting temperature regulator.

10. The method of claim 9, wherein the melting temperature regulator is at least one of the compounds selected from the group of betaine, proline, and dimethylsulfoxide.

11. The method of claim 1, wherein the nucleic acid sample is double stranded.

12. The method of claim 1, wherein the method is carried out in the presence of a nucleic acid detector to detect the presence of a mutation and/or polymorphism based on a change in the signal of the detector.

13. The method of claim 1, wherein a nucleotide sequence derived from the same organism as the organism for which a mutation and/or polymorphism is to be detected, and which sequence is confessed to include no mutation and/or polymorphism, is used as an internal standard, and the presence of a mutation and/or polymorphism is detected by comparing the amounts of synthesized products obtained using the nucleotide sequences as templates.

14. The method of claim 1, additionally comprising:

(h) a first loop primer, wherein the first loop primer provides an origin for complementary strand synthesis between a region originating from the first primer in the elongation product of the first primer and said arbitrary region for the first primer; and/or (i) a second loop primer, wherein the second loop primer provides an origin for complementary strand synthesis between a region originating from the second primer in the elongation product of the second primer and said arbitrary region for the second primer.

15. The method of claim 1, when the nucleotide sequence that comprises said specific region is not the predicted nucleotide sequence, a mismatch occurs during annealing to the specific region or the complementary strand thereof in the second to the fourth nucleotide from the 3'-end of the complementary strand which is synthesized using the nucleotide sequence arranged on the 5'-end of the first primer and/or second primer as the template.

16. A method for detecting mutations and/or polymorphisms in a specific region of a target nucleotide sequence, wherein the nucleotide sequence arranged on at least one of the 5'-ends of a second and first primer contains a nucleotide sequence that is complementary to the predicted nucleotide sequence of said specific region or the complementary strand thereof, and wherein the complementary strand, that is synthesized using the nucleotide sequence arranged on the 5'-end as the template and functions as the origin of complementary strand synthesis by annealing to the specific region or the complementary strand thereof, inhibits the complementary strand synthesis when the nucleotide sequence that contains the specific region is not a predicted one, which method comprises the steps of:

a) annealing a first primer to a target nucleotide sequence to carry out a complementary strand synthesis reaction using the primer as the origin, wherein the 3'-end of the first primer anneals to a 3'-side region of one of said target nucleotide sequence strands, and the 5'-side of the first primer includes a nucleotide sequence complementary to the predicted nucleotide sequence that contains a region on the product of the complementary strand synthesis reaction that uses the primer as the origin;

b) putting the region, to be annealed with the second primer, in the elongation product of the first primer synthesized in step a) into a state allowing base pairing of the region to the second primer, annealing them to synthesize the complementary strand using the elongation product of the first primer as a template; wherein the 3'-end of the second primer anneals to the 3'-side region of the other said target nucleotide sequence strand, and the 5'-side of the second primer includes a nucleotide sequence complementary to the predicted nucleotide sequence that contains a region on the product of the complementary strand synthesis reaction that uses the primer as the origin;

c) carrying out a complementary strand synthesis using the elongation product of the second primer itself as a template by annealing the 3'-end of the product with said predicted nucleotide sequence to the first primer in said elongation product;

d) carrying out a complementary strand synthesis using the complementary strand synthesized in step c) itself as a template by annealing the 3'-end of the complementary strand synthesized in step c) with said predicted nucleotide sequence to the second primer in said elongation product; and e) correlating the amount of synthesized product obtained using the second primer as the origin with the presence of a mutation and/or polymorphism in the specific region.

17. The method of claim 16, wherein step b) comprises a step of converting the elongation product of the first primer to a single strand by displacement, which displacement is conducted by a complementary strand synthesis reaction using the third primer that uses the 3'-side of the region annealing to the first primer in the template as the origin.

18. The method of claim 16, wherein step c) comprises a step of converting the elongation product of the second primer to a single strand by displacement, which displacement is conducted by a complementary strand synthesis reaction using the fourth primer that uses the 3'-side of the region annealing to the second primer in the template as the origin.

19. The method of claim 16, wherein the nucleotide sequence arranged on at least one of the 5'-ends of a second and first primer contains a nucleotide sequence that is complementary to the predicted nucleotide sequence of said specific region or to the complementary strand thereof, and wherein the complementary strand, that is synthesized using the nucleotide sequence arranged on the 5'-end as the template and functions as the origin of complementary strand synthesis by annealing to a specific region or the complementary strand thereof, inhibits the complementary strand synthesis when the nucleotide sequence that contains the specific region is not a predicted one, which method additionally comprises the steps of:

1) carrying out the complementary strand synthesis reaction of step (c) in the method of claim 16 by forming a loop forming region, that forms a base pair with a nucleotide sequence complementary to the 3'-end of the first primer, by annealing the 3'-end and the predicted nucleotide sequence within the elongation product of the second primer, and using the 3'-end of itself as the origin for the complementary strand synthesis;

2) annealing the first primer to the loop forming region, and carrying out complementary strand synthesis using the first primer as the origin with DNA polymerase catalyzing complementary strand synthesis which includes a strand displacement;

3) displacing the product elongated from its own 3'-end by a complementary strand synthesis reaction using a primer, that anneals to the loop forming region as the origin, to enable base pairing of the 3'-end and said predicted nucleotide sequence again;

4) forming a single stranded nucleic acid by displacing the complementary strand synthesized using the loop forming region as the origin by annealing the 3'-end, that was put in a state to form a base pair in step 3), to said predicted nucleotide sequence as the origin of the complementary strand synthesis to carry out a complementary strand synthesis reaction which uses itself as the template;

5) forming a loop forming region, that forms a base pair with a nucleotide sequence complementary to the 3'-end of the second primer, by annealing the 3'-end and said predicted nucleotide sequence for the second primer, and by complementary strand synthesis;

6) annealing the second primer to the loop forming region, and carrying out a complementary strand synthesis using the second primer as the origin by DNA polymerase catalyzing complementary strand synthesis including a strand displacement;

7) repeating steps 3) to 6); and 8) following step 7) and/or in parallel with step 7), detecting the formation of a single stranded nucleic acid, in which the target nucleotide sequence and the complementary strand thereof are repeatedly linked, and correlating the amount of formation with a mutation and/or polymorphism.

20. The method of claim 19, additionally comprising the steps of:

9) carrying out the complementary strand synthesis reaction using the single stranded nucleic acid formed in step 4) as the template by annealing the 3'-end thereof to said predicted nucleotide sequence for the second primer, forming a loop forming region, that forms a base pair with a nucleotide sequence complementary to the 3'-end of the second primer, and using the 3'-end of itself as the origin for the complementary strand synthesis;

10) annealing the second primer to the loop forming region, which region was formed by annealing the 3'-end with its own said specific region, and carrying out complementary strand synthesis using the second primer as the origin by DNA polymerase catalyzing complementary strand synthesis which includes a strand displacement;

11) displacing the product elongated from its own 3'-end by a complementary strand synthesis reaction using a primer, that anneals to the loop forming region as the origin, to enable base pairing of the 3'-end and said predicted nucleotide sequence again;

12) forming a single stranded nucleic acid by displacing the complementary strand synthesized using the loop forming region as the origin by annealing the 3'-end, that was put in a state to form a base pair in step 11), to said predicted nucleotide sequence as the origin of complementary strand synthesis to carry out a complementary strand synthesis reaction which uses itself as the template;

13) forming a loop forming region, that forms a base pair with a nucleotide sequence complementary to the 3'-end of the first primer, by annealing of the 3'-end and said predicted nucleotide sequence and carrying out complementary strand synthesis;

14) annealing the first primer to the loop forming region, and carrying out a complementary strand synthesis using the first primer as the origin by DNA polymerase catalyzing complementary strand synthesis which includes strand displacement;

15) repeating steps 11) to 14); and 16) following step 15) and/or in parallel with step 15), detecting the formation of a single stranded nucleic acid, in which the target nucleotide sequence and the complementary strand thereof are repeatedly linked, and correlating the amount of formation with a mutation and/or polymorphism.

21. The method of claim 20, additionally comprising the step of:

17) forming a loop forming region, that forms a base pair with a nucleotide sequence complementary to the 3'-end of the first primer, by annealing the 3'-end of the single stranded nucleic acid formed in step 12) with said predicted nucleic acid sequence on itself, and carrying out a complementary strand synthesis reaction using the 3'-end of itself as the origin and itself as the template.

22. The method of claim 16, wherein the nucleotide sequence arranged on the 5'-end of both of the second primer and first primer contains a nucleotide sequence complementary to the predicted nucleotide sequence of said specific region or the complementary strand thereof, and wherein the complementary strand, that is synthesized using the nucleotide sequence arranged on the 5'-end as the template and functions as the origin of complementary strand synthesis by annealing to the specific region or the complementary strand thereof, inhibits the complementary strand synthesis when the nucleotide sequence that contains the specific region is not a predicted one.

\* \* \* \* \*

UNITED STATES PATENT AND TRADEMARK OFFICE
CERTIFICATE OF CORRECTION

PATENT NO. : 7,175,985 B1  Page 1 of 1
APPLICATION NO. : 10/129637
DATED : February 13, 2007
INVENTOR(S) : Kanda et al.

It is certified that error appears in the above-identified patent and that said Letters Patent is hereby corrected as shown below:

Title page item (22) PCT Filed: delete "Aug. 2, 2002" and insert --Nov. 7, 2000--.

Signed and Sealed this

Twelfth Day of August, 2008

JON W. DUDAS
*Director of the United States Patent and Trademark Office*